(12) United States Patent
Yamashita et al.

(10) Patent No.: US 9,036,143 B2
(45) Date of Patent: May 19, 2015

(54) INSPECTION APPARATUS AND INSPECTION METHOD

(71) Applicant: NuFlare Technology, Inc., Yokohama (JP)

(72) Inventors: Yasuhiro Yamashita, Kanagawa (JP); Riki Ogawa, Kanagawa (JP); Toshiaki Otaki, Kanagawa (JP)

(73) Assignee: NuFlare Technology, Inc., Yokohama (JP)

( * ) Notice: Subject to any disclaimer, the term of this patent is extended or adjusted under 35 U.S.C. 154(b) by 0 days.

(21) Appl. No.: 14/251,718

(22) Filed: Apr. 14, 2014

(65) Prior Publication Data

US 2014/0307254 A1 Oct. 16, 2014

(30) Foreign Application Priority Data

Apr. 16, 2013 (JP) ................................. 2013-086107

(51) Int. Cl.
*G01N 21/956* (2006.01)
*G06T 7/00* (2006.01)

(52) U.S. Cl.
CPC .......... *G01N 21/95607* (2013.01); *G06T 7/001* (2013.01); *G01N 2021/95615* (2013.01); *G01N 2021/95676* (2013.01); *G06T 2207/30148* (2013.01)

(58) Field of Classification Search
CPC .............. G01N 21/95607; G01N 2021/95615; G01N 2021/95676; G06T 7/001; G06T 2207/30148

USPC ............ 356/237.1–237.5; 382/144, 145, 149, 382/154

See application file for complete search history.

(56) References Cited

U.S. PATENT DOCUMENTS

| | | | |
|---|---|---|---|
| 8,903,158 B2 * | 12/2014 | Tsuchiya et al. ............... | 382/149 |
| 2004/0262529 A1 * | 12/2004 | Yoshida et al. ................ | 250/372 |
| 2005/0052634 A1 * | 3/2005 | Sugihara et al. ................ | 355/55 |
| 2005/0110988 A1 * | 5/2005 | Nishiyama et al. ......... | 356/237.5 |
| 2009/0237909 A1 * | 9/2009 | Ogawa ............................ | 362/19 |
| 2013/0336574 A1 * | 12/2013 | Nasser-Ghodsi et al. ..... | 382/145 |
| 2013/0343632 A1 * | 12/2013 | Urano et al. ................... | 382/149 |

FOREIGN PATENT DOCUMENTS

JP 4236825 3/2009

* cited by examiner

*Primary Examiner* — Sang Nguyen
(74) *Attorney, Agent, or Firm* — Oblon, McClelland, Maier & Neustadt, L.L.P.

(57) ABSTRACT

An inspection apparatus comprising, a Rochon prism configured to branch the light transmitted through a half-wave plate, a first sensor and a second sensor for acquiring an optical image of a pattern of the sample, the branched light being incident to the first sensor and the second sensor, a light quantity acquisition unit configured to acquire a light quantity ratio (1:A) of the second sensor to the first sensor using the optical image, and to obtain an angle θ of the half-wave plate such that the light quantity ratio becomes A:1, an angle controller configured to receive information on the angle θ from the light quantity acquisition unit to control an angle of the half-wave plate, a light source controller configured to control a light quantity of the light source such that each of the light quantity values becomes a target value.

8 Claims, 15 Drawing Sheets

INSPECTION APPARATUS AND INSPECTION METHOD

CROSS-REFERENCE TO THE RELATED APPLICATION

The entire disclosure of the Japanese Patent Application No. 2013-086107, filed on Apr. 16, 2013 including specification, claims, drawings, and summary, on which the Convention priority of the present application is based, are incorporated herein in its entirety.

FIELD OF THE INVENTION

The present invention relates to an inspection apparatus and inspection Method.

BACKGROUND

Recently, with increasing integration degree of a semiconductor device, dimensions of individual element become finer, and widths of wiring and gate constituting each element also become finer.

A process of transferring an original plate (a mask or a reticle, hereinafter collectively referred to as a mask) to a photosensitive resin to fabricate a wafer is fundamental to production of a semiconductor integrated circuit. The semiconductor integrated circuit is produced by repeating the fundamental process.

An exposure apparatus called a stepper or a scanner is used in the transfer process. In the exposure apparatus, light is used as a transfer light source, a circuit pattern on the reticle is projected onto the wafer while reduced to about one-fourth to about one-fifth. In order to increase the integration degree of the semiconductor integrated circuit, it is necessary to improve resolution performance in the transfer process. Assuming that NA is an aperture factor of an imaging optical system, and that $\lambda$ is a wavelength of the light source, a resolution dimension is proportional to ($\lambda$/NA). Accordingly, higher exposure resolution can be achieved by increasing the aperture factor NA or decreasing the wavelength $\lambda$.

Nowadays, an EUV (Extreme Ultra Violet) lithography technology in which EUV light having the short wavelength ($\lambda$=13 to 14 nm) is used is being developed. Although the aperture factor NA of EUV lithography is smaller than that of photolithography, the circuit pattern is resolved by about 1.5 times to about 2.0 times of the wavelength in the EUV lithography. Therefore, the resolution dimension of 30 nm or less can be obtained.

Because a large cost is imposed on the production of the semiconductor integrated circuit, it is necessary to improve a yield. A defect of a mask pattern can be cited as one of large factors that degrade the yield. Therefore, in a mask inspection, it is necessary to detect the extremely small pattern defect. Japanese Patent No. 4236825 discloses an inspection apparatus that can detect the fine defect on the mask.

In the mask inspection, the mask is illuminated with the light while moved, and the pattern formed on the mask is imaged with an imaging element. Then, an obtained optical image is compared to a standard image, and a place where a difference between the optical image and the standard image exceeds a threshold is detected as the defect.

A density of the pattern formed on the mask is not constant. Such a region as a memory mat portion of a semiconductor chip, where the pattern density is high, and such a region as a peripheral circuit portion of the semiconductor chip, where the pattern density is low, are mixed in the pattern.

FIG. 1 is a schematic sectional view of the mask, and illustrates a state in which a patterned film 92 such as a chromium (Cr) film is provided on a glass substrate 91. In FIG. 1, a region A is a coarse pattern area and a region B is a dense pattern area. FIG. 2 illustrates a light quantity value of the light incident to a TDI (Time Delay Integration) sensor when the pattern in FIG. 1 is imaged with the TDI sensor along an X-axis direction. As illustrated in FIG. 2, the region A having the low pattern density has the large light quantity value, and is brightly observed on the mask. On the other hand, the region B having the high pattern density has the low light quantity value, and is darkly observed on the mask. Therefore, although the high-contrast image is obtained in the region A, the high-contrast image is not obtained in the region B, but a noise increases to degrade inspection accuracy. On the other hand, when the quantity of light with which the mask is illuminated increases to obtain the high-contrast image in the region B, unfortunately the quantity of light incident to the sensor increases excessively in the region A and the sensor reaches a saturated state.

The similar problem is generated in an EUV mask.

FIG. 3 is a schematic sectional view of the EUV mask. As illustrated in FIG. 3, in the EUV mask, a multilayer film 94 that is made of molybdenum and silicon while constructed with a predetermined number of layers is stacked on a glass substrate 93 to form a reflecting layer. A patterned film 95 is provided on the multilayer film 94. The film 95 is an absorbing layer made of a material having a high absorption coefficient with respect to the EUV light. A buffer film (not illustrated) is provided between the multilayer film 94 and the film 95. The buffer film reduces damage to the multilayer film 94 in patterning the film 95 or correcting the defect.

In FIG. 3, the region A is the coarse pattern area and the region B is the dense pattern area. FIG. 4 illustrates the light quantity value of the light incident to the TDI sensor when the pattern in FIG. 3 is imaged with the TDI sensor along the X-axis direction. As illustrated in FIG. 4, the region A having the low pattern density is brightly observed on the mask, and the region B having the high pattern density is darkly observed on the mask. Therefore, similarly to the example in FIG. 1, there is generated the problem in that the inspection accuracy is degraded in the region B. When the quantity of light with which the mask is illuminated increases, the quantity of light incident to the sensor increases excessively in the region A and the sensor reaches the saturated state.

The EUV mask in FIG. 3 is more noticeable than the mask in FIG. 1 in a light quantity difference between the region A and the region B. The following items are cited as the main reason. That is, 1) the multilayer film 94 is provided on the glass substrate 93, and 2) the pattern in the EUV mask is largely influenced by diffraction because the pattern in the EUV mask is finer than that of the mask in FIG. 1.

Therefore, there is a strong demand to develop the inspection apparatus and inspection method for being able to accurately inspect the mask, particularly the EUV mask. An object of the present invention is to provide an inspection apparatus and an inspection method for being able to accurately inspect both the region having the high pattern density and the region having the low pattern density.

Other challenges and advantages of the present invention are apparent from the following description.

SUMMARY OF THE INVENTION

According to one aspect of the present invention, an inspection apparatus comprising, a light source configured to emit light with which a sample is illuminated, a half-wave plate configured to transmit the light emitted from the light source, a branching element configured to branch the light transmitted through the half-wave plate, a first sensor and a second sensor configured to acquire an optical image of a pattern formed in the sample, sensing the branched light incident on the first sensor and the second sensor, a light quantity acquisition unit configured to acquire a light quantity ratio (1:A) of the second sensor to the first sensor using the optical image, and to obtain an angle θ of the half-wave plate such that the light quantity ratio becomes A:1, an angle controller configured to receive information on the angle θ from the light quantity acquisition unit to control an angle of the half-wave plate, a light source controller configured to receive information on each of light quantity values of the first sensor and the second sensor from the light quantity acquisition unit, and to control a light quantity of the light source such that each of the light quantity values becomes a target value, and a comparator configured to compare the optical image acquired by the first sensor to a standard image with respect to a pattern having a density of a predetermined value or more in the pattern, to compare the optical image acquired by the second sensor to the standard image with respect to a pattern having a density smaller than the predetermined value in the pattern, and to determine a place where a difference between the optical image acquired by the first sensor and the standard image or a difference between the optical image acquired by the second sensor and the standard image exceeds a threshold to be a defect.

Further to this aspect of the present invention, an inspection apparatus, wherein the branching element branches the light with which the sample is illuminated.

Further to this aspect of the present invention, an inspection apparatus, further comprising a quarter-wave plate, wherein the sample is illuminated with the light, which is transmitted through the quarter-wave plate after transmitted through the branching element.

Further to this aspect of the present invention, an inspection apparatus, wherein the branching element branches the light reflected by or transmitted through the sample.

Further to this aspect of the present invention, an inspection apparatus, wherein the half-wave plate transmits the light reflected by or transmitted through the sample.

Further to this aspect of the present invention, an inspection apparatus, wherein the half-wave plate, the branching element, and the quarter-wave plate are configured to be detachable.

In another aspect of the present invention, an inspection method comprising the steps of, illuminating a sample with light, which is emitted from a light source and transmitted through a half-wave plate, after the light is branched, causing the light reflected by or transmitted through the sample to impinge on a first sensor and a second sensor, and adjusting a light quantity of the light source (1) when a light quantity of the first sensor reaches saturation or (2) when a light quantity of the second sensor is lower than a predetermined value, acquiring an optical image of a pattern formed in the sample using the first sensor and the second sensor when both the condition (1) and the condition (2) are not satisfied, acquiring a light quantity ratio (1:A) of the second sensor to the first sensor using the optical image, and obtaining an angle θ of the half-wave plate such that the light quantity ratio becomes A:1, adjusting an angle of the half-wave plate to the angle θ, controlling the light quantity of the light source such that each of light quantity values of the first sensor and the second sensor becomes a target value, acquiring the optical image of the pattern formed in the sample using the first sensor and the second sensor after the angle of the half-wave plate is adjusted to the angle θ and after each of the light quantity values of the first sensor and the second sensor becomes the target value, and comparing the optical image acquired by the first sensor to a standard image with respect to a pattern having a density of a predetermined value or more in the pattern, comparing the optical image acquired by the second sensor to the standard image with respect to a pattern having a density smaller than the predetermined value in the pattern, and determining a place where a difference between the optical image acquired by the first sensor and the standard image or a difference between the optical image acquired by the second sensor and the standard image exceeds a threshold to be a defect.

In another aspect of the present invention, an inspection method comprising, illuminating a sample with light emitted from a light source, causing the light to impinge on a first sensor and a second sensor after the light, which is reflected by or transmitted through the sample and transmitted through a half-wave plate, is branched, and adjusting a light quantity of the light source (1) when a light quantity of the first sensor reaches saturation or (2) when a light quantity of the second sensor is lower than a predetermined value, acquiring an optical image of a pattern formed in the sample using the first sensor and the second sensor when both the condition (1) and the condition (2) are not satisfied, acquiring a light quantity ratio (1:A) of the second sensor to the first sensor using the optical image, and obtaining an angle θ of the half-wave plate such that the light quantity ratio becomes A:1, adjusting an angle of the half-wave plate to the angle θ, controlling the light quantity of the light source such that each of light quantity values of the first sensor and the second sensor becomes a target value, acquiring the optical image of the pattern formed in the sample using the first sensor and the second sensor after the angle of the half-wave plate is adjusted to the angle θ and after each of the light quantity values of the first sensor and the second sensor becomes the target value, and comparing the optical image acquired by the first sensor to a standard image with respect to a pattern having a density of a predetermined value or more in the pattern, comparing the optical image acquired by the second sensor to the standard image with respect to a pattern having a density smaller than the predetermined value in the pattern, and determining a place where a difference between the optical image acquired by the first sensor and the standard image or a difference between the optical image acquired by the second sensor and the standard image exceeds a threshold to be a defect.

DETAILED DESCRIPTION OF THE EMBODIMENTS

One of a die-to-database comparison method, a die-to-die comparison method, and a cell comparison method may be used as the inspection method of the present invention, and a method for comparing an interesting pixel in one image to a peripheral pixel may be used like a template inspection of Nanoimprint Lithography (NIL). Hereinafter, the die-to-database comparison method is described by way of example. In the die-to-database comparison method, a reference image produced from design data for a pattern of an inspection target becomes a standard image, namely, an image that is compared to an optical image of the pattern in order to detect a defect.

First Embodiment

Figure 5:
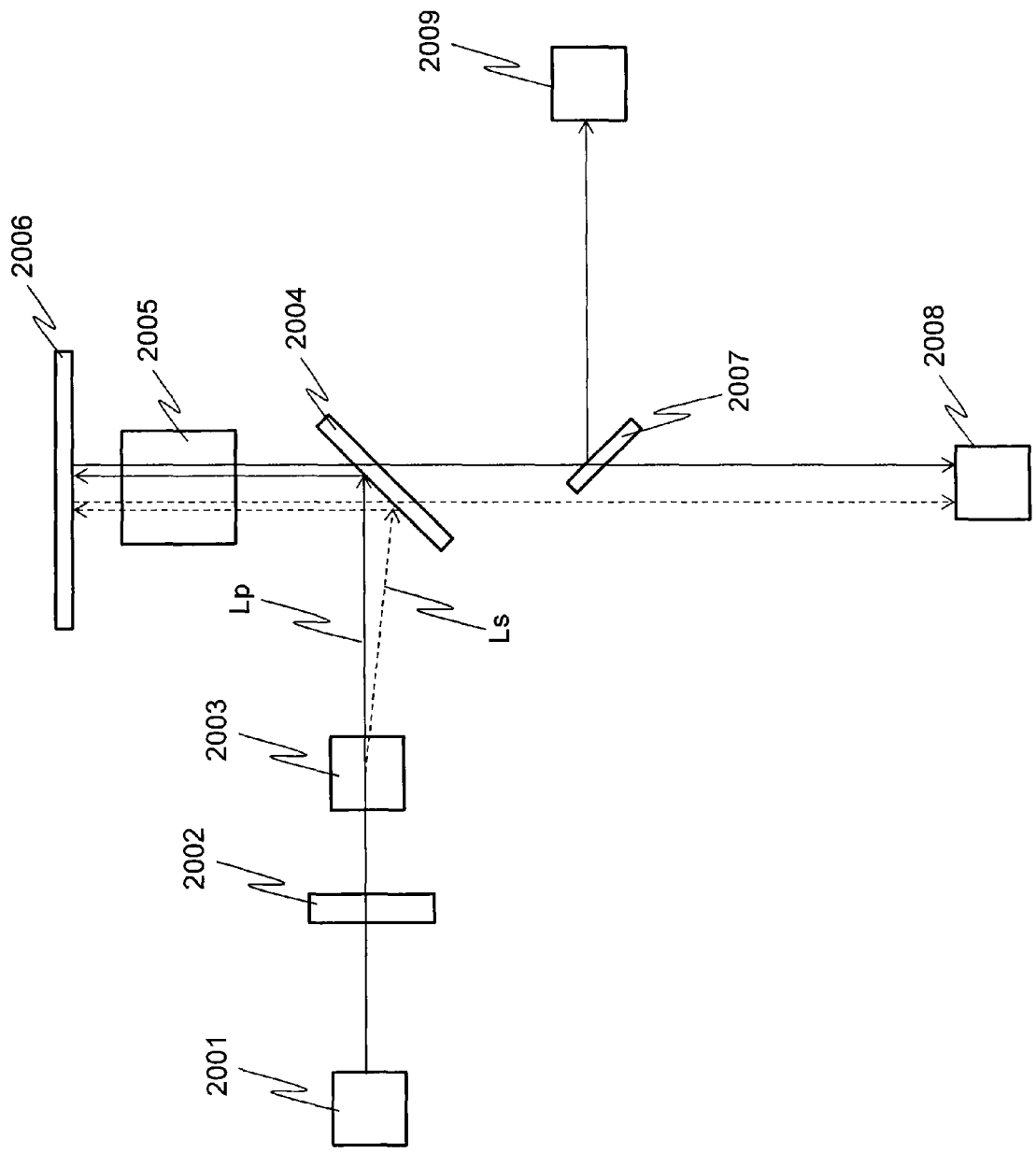
FIG. 5 is a schematic view illustrating a configuration of an optical system according to an inspection apparatus of the first embodiment.

FIG. 5 is a schematic view illustrating a configuration of an optical system in an inspection apparatus according to a first embodiment.

An illumination optical system will be described below. A laser beam source can be used as a light source 2001 in FIG. 5. Generally linearly-polarized light is emitted from the laser beam source. After a phase of the linearly-polarized light is rotated by 90° using a half-wave plate 2002, the linearly-polarized light is incident to a Rochon prism 2003 that is of the branching element. At this point, an angle of the half-wave plate 2002 is set such that a quantity of p-polarized light (Lp) incident to the Rochon prism 2003 is equal to a quantity of s-polarized light (Ls) incident to the Rochon prism 2003. Although the Rochon prism 2003 transmits a p-polarized light component (Lp) straight, the Rochon prism 2003 transmits an s-polarized light component (Ls) while displacing the s-polarized light component from an original optical axis. A polarizing prism except the Rochon prism 2003 may be used as the branching element of the first embodiment as long as the polarizing prism branches polarized light components orthogonal to each other into two.

After the light transmitted through the Rochon prism 2003 is reflected by a half mirror 2004, a mask 2006 that is the inspection target is illuminated with the light through an objective lens 2005. Then the light reflected by the mask 2006 is incident to an imaging optical system through the objective lens 2005 and the half mirror 2004.

In FIG. 5, two sensors 2008 and 2009 are provided as the imaging element in the imaging optical system. For example, a TDI (Time Delay Integration) sensor can be used as the sensor.

The s-polarized light (Ls) reflected by the mask 2006 is incident to the first sensor 2008. On the other hand, an optical path of the p-polarized light (Lp) reflected by the mask 2006 is changed by a half mirror 2007, and the p-polarized light (Lp) is incident to the second sensor 2009.

Figure 3:
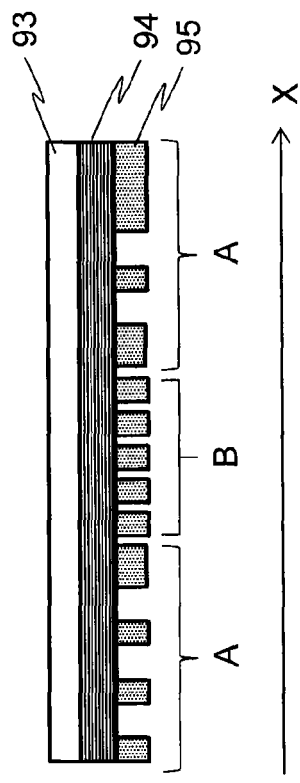
FIG. 3 is a schematic sectional view of an EUV mask.
Figure 4:
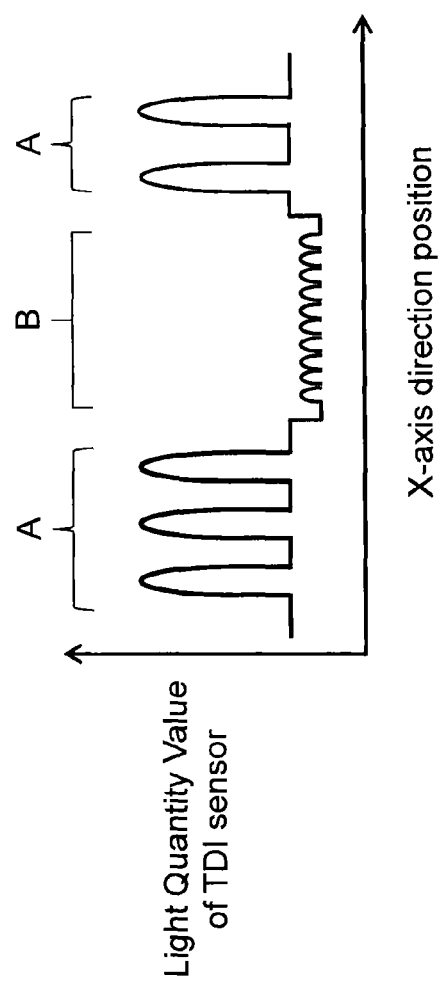
FIG. 4 illustrates a light quantity value of light incident to a TDI sensor when the pattern of FIG. 3 is imaged along an X-axis direction.

The mask 2006 is the EUV mask in FIG. 3. The mask that is of the inspection target is not limited to the EUV mask. For example, the mask may have the configuration in FIG. 1.

In the mask 2006, a reflecting layer is formed on a glass substrate, and a patterned absorbing layer is formed on the reflecting layer. For example, a multilayer film that is made of molybdenum and silicon while constructed with a predetermined number of layers is stacked in the reflecting layer. The absorbing layer is made of a material having a high absorption coefficient with respect to the EUV light. A buffer film may be provided between the reflecting layer and the absorbing layer. The buffer film can reduce damage to the reflecting layer in patterning the absorbing layer or correcting the defect.

The first and second sensors 2008 and 2009 in FIG. 5 image the same mask 2006. At this point, the pattern of the absorbing layer has the dense pattern area and the coarse pattern area as illustrated in FIG. 3. As to definitions of the dense pattern and the coarse pattern, for example, a pattern density that is a threshold is previously fixed, the pattern having the pattern density or more is defined as the dense pattern, and the pattern having the density less than the pattern density is defined as the coarse pattern (same as in the present specification).

In the first embodiment, according to the following method, the first sensor 2008 images the pattern with a light quantity value suitable for the dense pattern area. The second sensor 2009 images the pattern with a light quantity value suitable for the coarse pattern area. Specifically, the imaging is performed with the first and second sensors 2008 and 2009 by adjusting a light quantity of the light source 2001 and an angle of the half-wave plate 2002.

Figure 6:
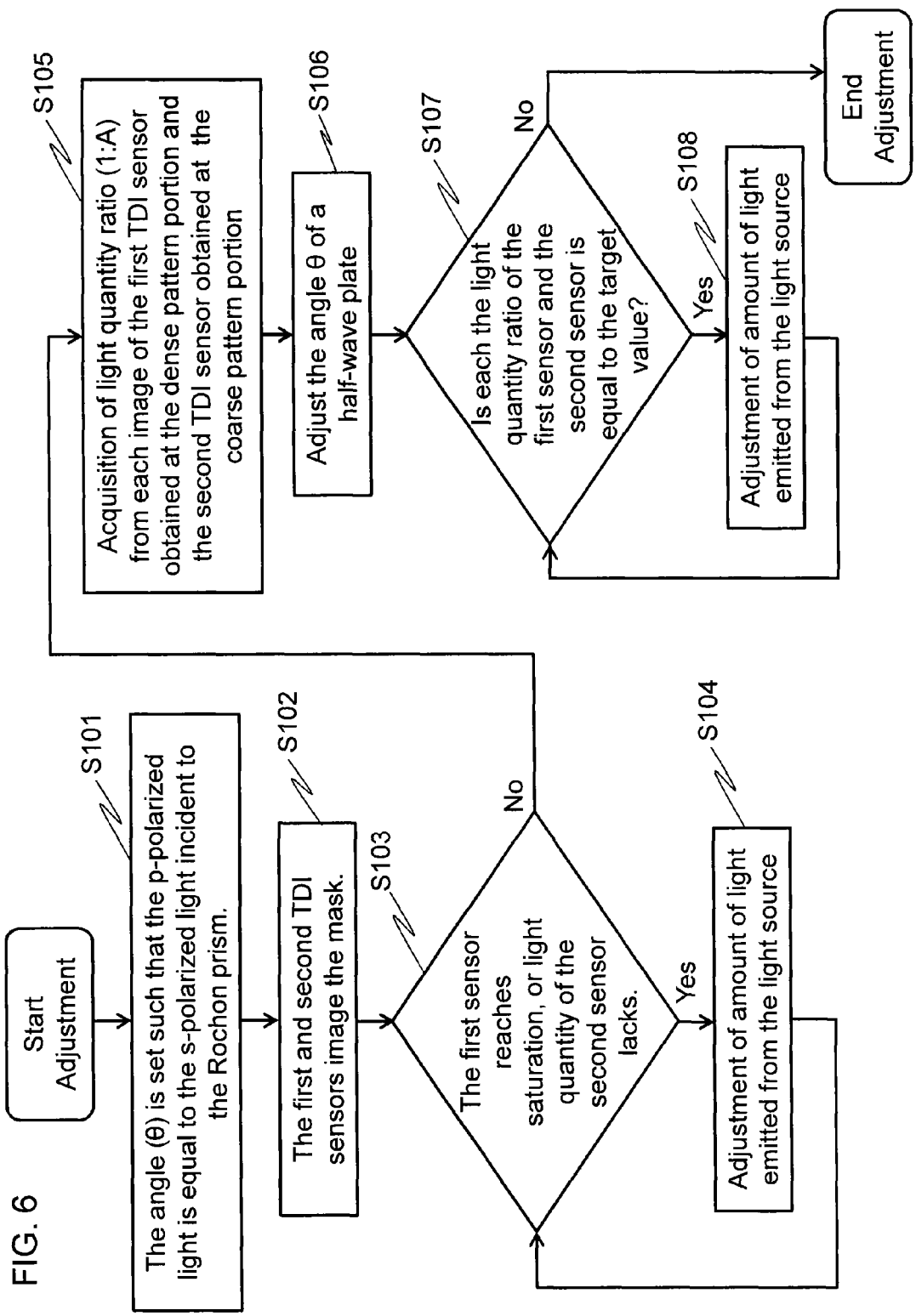
FIG. 6 is a flowchart illustrating a method for adjusting light quantity of a light source and angle of a half-wave plate according to the first embodiment.

FIG. 6 is a flowchart illustrating a method for adjusting the light quantity of the light source 2001 and the angle of the half-wave plate 2002, and the method is a substantial part of the inspection method of the first embodiment.

Referring to FIG. 6, in S101, the angle of the half-wave plate 2002 is set such that the quantity of p-polarized light (Lp) incident to the Rochon prism 2003 in FIG. 5 is equal to the quantity of s-polarized light (Ls) incident to the Rochon prism 2003.

The first and second sensors 2008 and 2009 image the pattern of the mask 2006 (S102).

(1) Whether the light quantity value of the first sensor 2008 reaches the saturation, or (2) whether the light quantity value of the second sensor 2009 is lacking, namely, whether the light quantity value of the second sensor 2009 does not reach the value enough to obtain the sufficient contrast is determined irrespective of the dense or coarse pattern (S103). When one of the conditions (1) and (2) is satisfied, the flow goes to S104 to adjust the light quantity introduced to the optical system from the light source 2001. Then, the flow returns to S103, and the processes in S103 and S104 are repeated until both the conditions (1) and (2) are not satisfied.

When both the conditions (1) and (2) are not satisfied in S103, the flow goes to S105.

Figure 7:
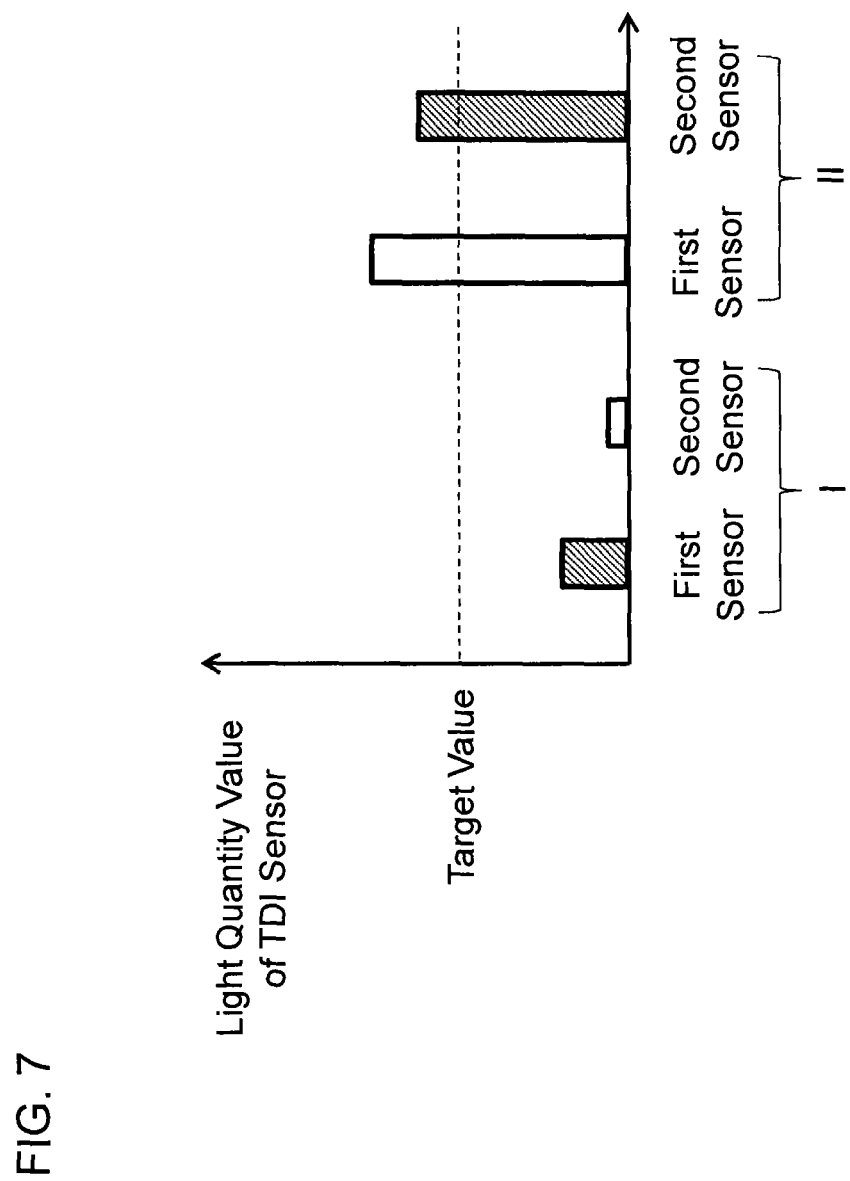
FIG. 7 illustrates an example of a relationship between the first and second sensors and a light quantity value.

FIG. 7 illustrates an example of a relationship between the first and second sensors 2008 and 2009 and the light quantity value. In FIG. 7, a target value is the light quantity value in which the contrast suitable for the inspection is obtained. In FIG. 7, (I) indicates the light quantity value when the dense pattern area of the mask 2006 is imaged and (II) indicates the light quantity value when the coarse pattern area of the mask 2006 is imaged.

In S105, a light quantity ratio (1/A) of the second sensor 2009 to the first sensor 2008 is obtained from the dense pattern area imaged with the first sensor 2008 and the coarse pattern area imaged with the second sensor 2009.

Figure 8:
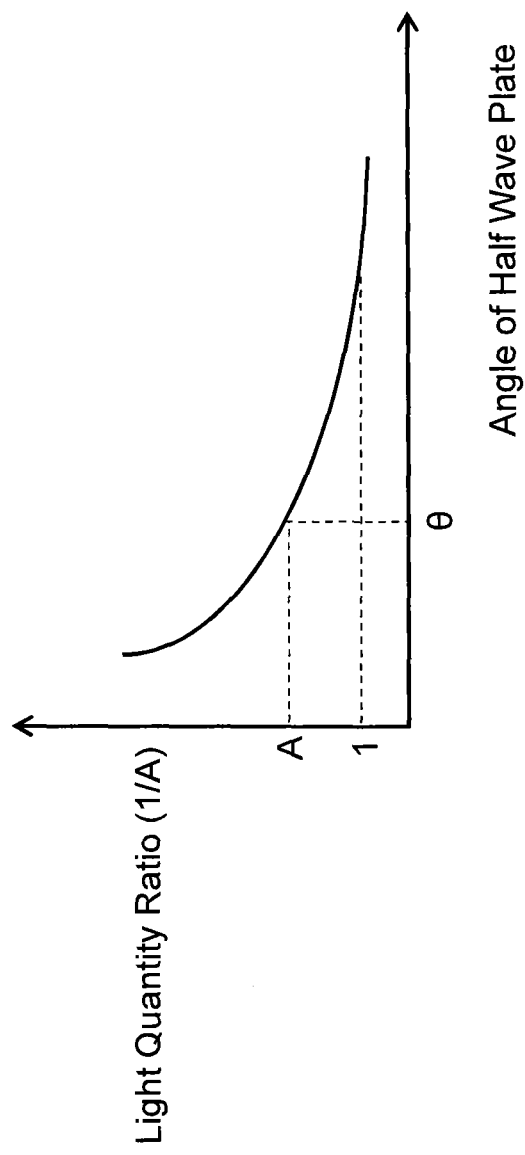
FIG. 8 illustrates an example of a relationship between angle of the half-wave plate and light quantity ratio (1/A).

FIG. 8 illustrates an example of a relationship between the angle of the half-wave plate 2002 and the light quantity ratio (1/A). Using the relationship in FIG. 8, the angle of the half-wave plate 2002 is adjusted to an angle θ such that the light quantity ratio of the second sensor 2009 to the first sensor 2008 becomes A:1 (S106).

Figure 9:
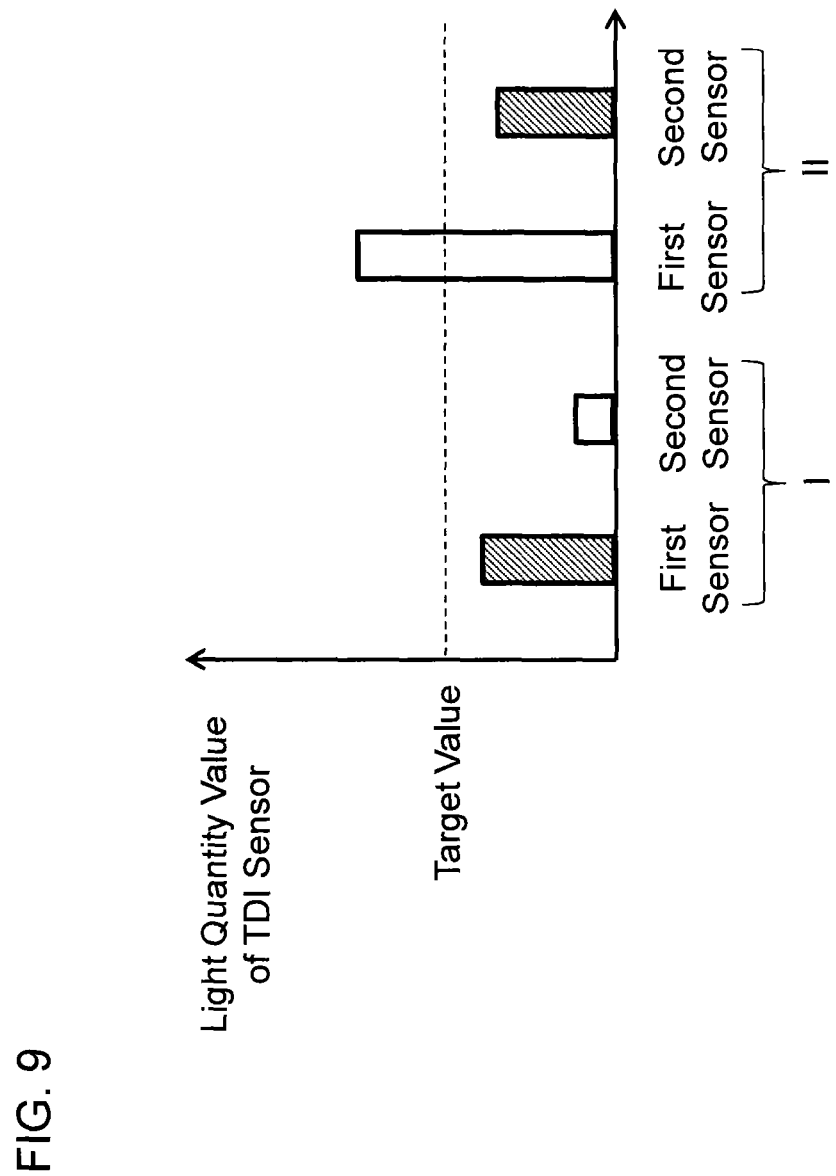
FIG. 9 illustrates an example of a relationship between each sensor and the light quantity value after the angle of the half-wave plate is adjusted to the angle θ.

FIG. 9 illustrates an example of a relationship between each sensor and the light quantity value after the angle of the half-wave plate 2002 is adjusted to the angle θ in S106. As a result of the determination in S107, when each of the light quantity values of the first and second sensors 2008 and 2009 is much larger or smaller than the target value, the flow goes to S108 to adjust the light quantity introduced to the optical system from the light source 2001. Then, the flow returns to S107, and the processes in S107 and S108 are repeated until each light quantity value reaches the target value.

Figure 10:
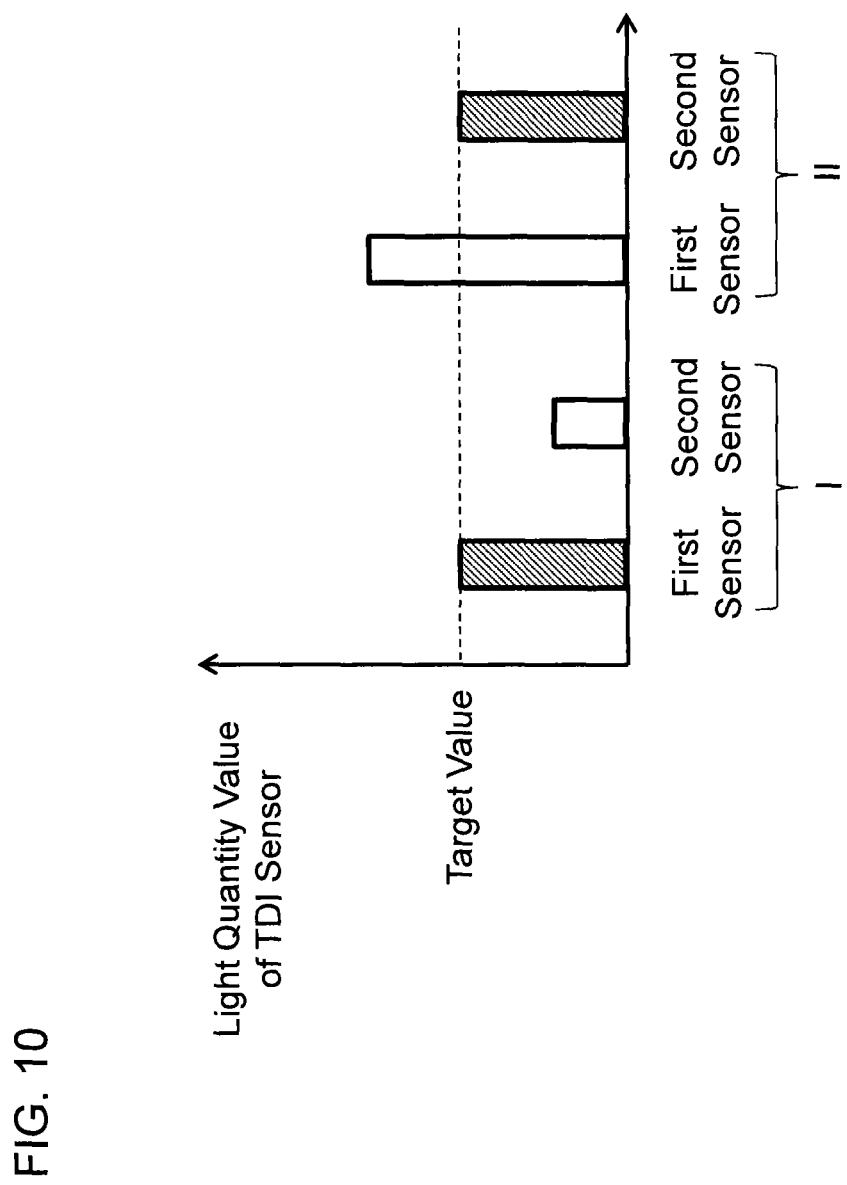
FIG. 10 illustrates an example in which the light quantity value of the first sensor and the light quantity value of the second sensor reach the target value.

A series of adjusting processes is ended after the light quantity value in the dense pattern area at the first sensor 2008 and the light quantity value in the coarse pattern area at the second sensor 2009 reach the target value as illustrated in FIG. 10.

Through the above processes, the first sensor 2008 can image the pattern with the light quantity value suitable for the dense pattern area. The second sensor 2009 can image the pattern with the light quantity value suitable for the coarse pattern area.

An inspection apparatus according to the present embodiment will be described below.

Figure 11:
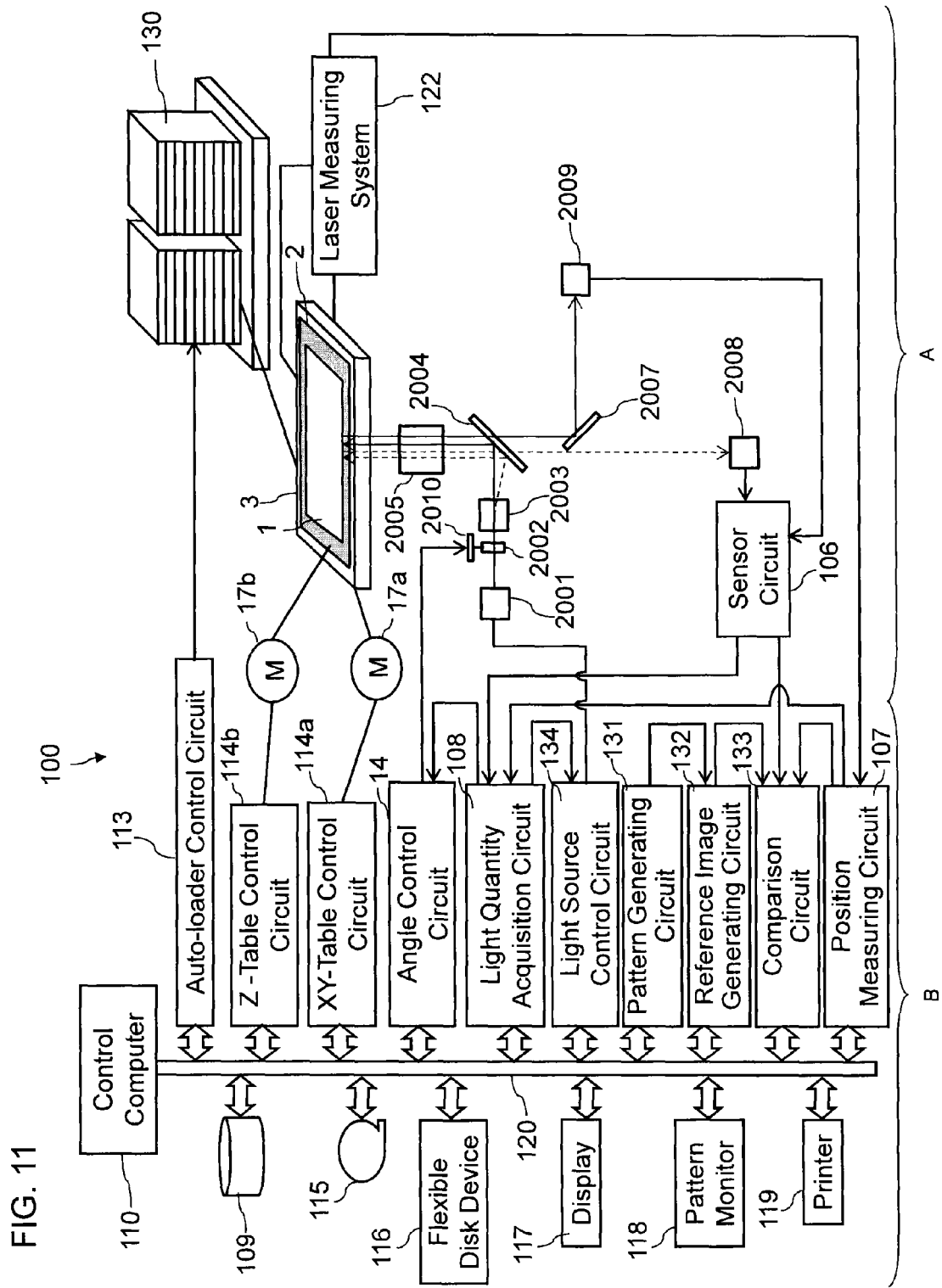
FIG. 11 is a configuration diagram of the inspection apparatus according to the first embodiment.

FIG. 11 is a configuration diagram of an inspection apparatus 100 according to the present embodiment. As shown in FIG. 11, the inspection apparatus 100 includes a configuration unit A that constitutes an optical image acquisition unit and a configuration unit B that performs processing necessary for an inspection using an optical image acquired by the configuration unit A.

The configuration unit A includes the optical system as shown in FIG. 5. Further, it includes an XY-table 3 that is movable in a horizontal direction (an X direction and a Y direction), a sensor circuit 106, a laser measuring system 122, and an auto-loader 130. The XY-table 3 may have a structure movable in a rotation direction.

In the configuration unit A, an optical image data of the sample 1 that is an inspection target is acquired. The optical image data is an image of a mask in which a figure pattern is written based on graphic data included in design pattern data of the sample 1. For example, the optical image data is 8-bit data with no code, and expresses a gradation of brightness of each pixel.

A sample 1 that is the inspection target is placed on a Z-table 2. The Z-table 2 is provided on the XY-table 3, and is horizontally movable together with the XY-table 3. The mask or the wafer may be used as the sample 1. In the present invention, the EUV mask is particularly suitable for the sample 1. A predetermined pattern such as a line and space pattern is provided in the sample 1. In the case that the sample 1 is the EUV mask in FIG. 3, the absorbing layer (the film 95) on the reflecting layer (the multilayer film 94) is the patterned layer. The density of the pattern provided in the sample 1 is not constant. Such a region as a memory mat portion of a semiconductor chip, where the pattern density is high, and such a region as a peripheral circuit portion of the semiconductor chip, where the pattern density is low, are mixed in the pattern.

Preferably the sample 1 is supported at three points using support members provided in the Z-table 2. In the case that the sample 1 is supported at four points, it is necessary to adjust a height of the support member with high accuracy. Unless the height of the support member is sufficiently adjusted, there is a risk of deforming the sample 1. On the other hand, in the three-point support, the sample 1 can be supported while the deformation of the sample 1 is suppressed to the minimum. The supporting member is configured by using a ballpoint having a spherical head surface. For example, the two support members in the three support members are in contact with the sample 1 at two corners, which are not diagonal but adjacent to each other in four corners of the sample 1. The remaining support member in the three support members is disposed in the region between the two corners at which the two other support members are not disposed.

The light source 2001 emits the light to the sample 1 in order to acquire the optical image of the sample 1. For example, a laser beam source that emits linearly-polarized light can be used as the light source 2001.

The linearly-polarized light emitted from the light source 2001 is incident to the Rochon prism 2003 while the phase of the linearly-polarized light is rotated by 90° using the half-wave plate 2002. Although the Rochon prism 2003 transmits the p-polarized light component (Lp) straight, the Rochon prism 2003 transmits the s-polarized light component (Ls) while displacing the s-polarized light component from the original optical axis. The polarizing prism except the Rochon prism 2003 may be used as long as the polarizing prism branches the polarized light components orthogonal to each other into two.

After the light transmitted through the Rochon prism 2003 is reflected by the half mirror 2004, the sample 1 is illuminated with the light through the objective lens 2005. Then the light reflected by the sample 1 is incident to the imaging optical system through the objective lens 2005 and the half mirror 2004.

The first and second sensors 2008 and 2009 are provided as the imaging element in the imaging optical system. A line sensor in which CCD cameras are arrayed in line is used as the first and second sensors 2008 and 2009. The TDI sensor can be cited as an example of the line sensor. The s-polarized light (Ls) reflected by the sample 1 is incident to the first sensor 2008. On the other hand, the optical path of the p-polarized light (Lp) reflected by the sample 1 is changed by the half mirror 2007, and the p-polarized light (Lp) is incident to the second sensor 2009.

In the above optical system, the light reflected by the sample 1 is introduced to the sensor. Alternatively, the sample 1 is illuminated with the light from above, and the light transmitted through the sample 1 may be introduced to the sensor. A combination of the both can simultaneously obtain the optical images of the transmitted light and the reflected light.

In the configuration unit B, a control computer 110 that controls the whole inspection apparatus 100 is connected to a position measuring circuit 107, a light quantity acquisition circuit 108 used as an example of a light quantity acquisition unit, an angle control circuit 14, an pattern generating circuit 131, a reference image generating circuit 132, a comparison circuit 133, a light source control circuit 134 used as an example of a light source controller, an auto-loader control circuit 113, a XY-table control circuit 114a and a Z-table control circuit 114b, a magnetic disk device 109, a magnetic tape device 115, and flexible disk device 116, which are examples of a storage device, a display 117, a pattern monitor 118, and a printer 119 through a bus 120 that constitutes a data transmission line.

In FIG. 11, the position measuring circuit 107, the light quantity acquisition circuit 108, the angle control circuit 14, the pattern generating circuit 131, the reference image generating circuit 132, the comparison circuit 133, the light source control circuit 134, the auto-loader control circuit 113, an XY-table control circuit 114a, and a Z-table control circuit 114b are constructed with electric circuits. However, the inspection apparatus 100 is not necessarily constructed with the electric circuits. Alternatively, at least some of the electric circuits may be replaced with software that can cause the control computer 110 to execute the similar processing. The inspection apparatus 100 may be constructed with a combination of the electric circuits and the software. As used herein, the "unit" is a concept including the "circuit", and may be constructed with a program running on a computer, a combination of hardware and software, or a combination of software and firmware as well as a program being software. In the case that the unit is constructed with the program, the program is recorded, for example, in the magnetic disk device 109.

The Z-table 2 is driven by the motor 17b controlled by the Z-table control circuit 114b. The XY-table 3 is driven by the motor 17a controlled by the XY-table control circuit 114a. For example, a stepping motor is used as each motor.

The control computer 110 controls the XY-table control circuit 114a and Z-table control circuit 114b to drive the XY-table 3 and Z-table 2. A moving position of the XY-table 3 is measured by the laser measuring system 122, and transmitted to the position measuring circuit 107.

The control computer 110 controls the auto-loader control circuit 113 to drive the auto-loader 130. The auto-loader 130 automatically conveys the sample 1, and automatically discharges the sample 1 after the inspection.

The design pattern data that is reference data of the die-to-database method is stored in the magnetic disk drive 109. In the progress of the inspection, the design pattern data is read and transmitted to the pattern generating circuit 131. The design pattern data will be described with reference to FIG. 12.

Figure 12:
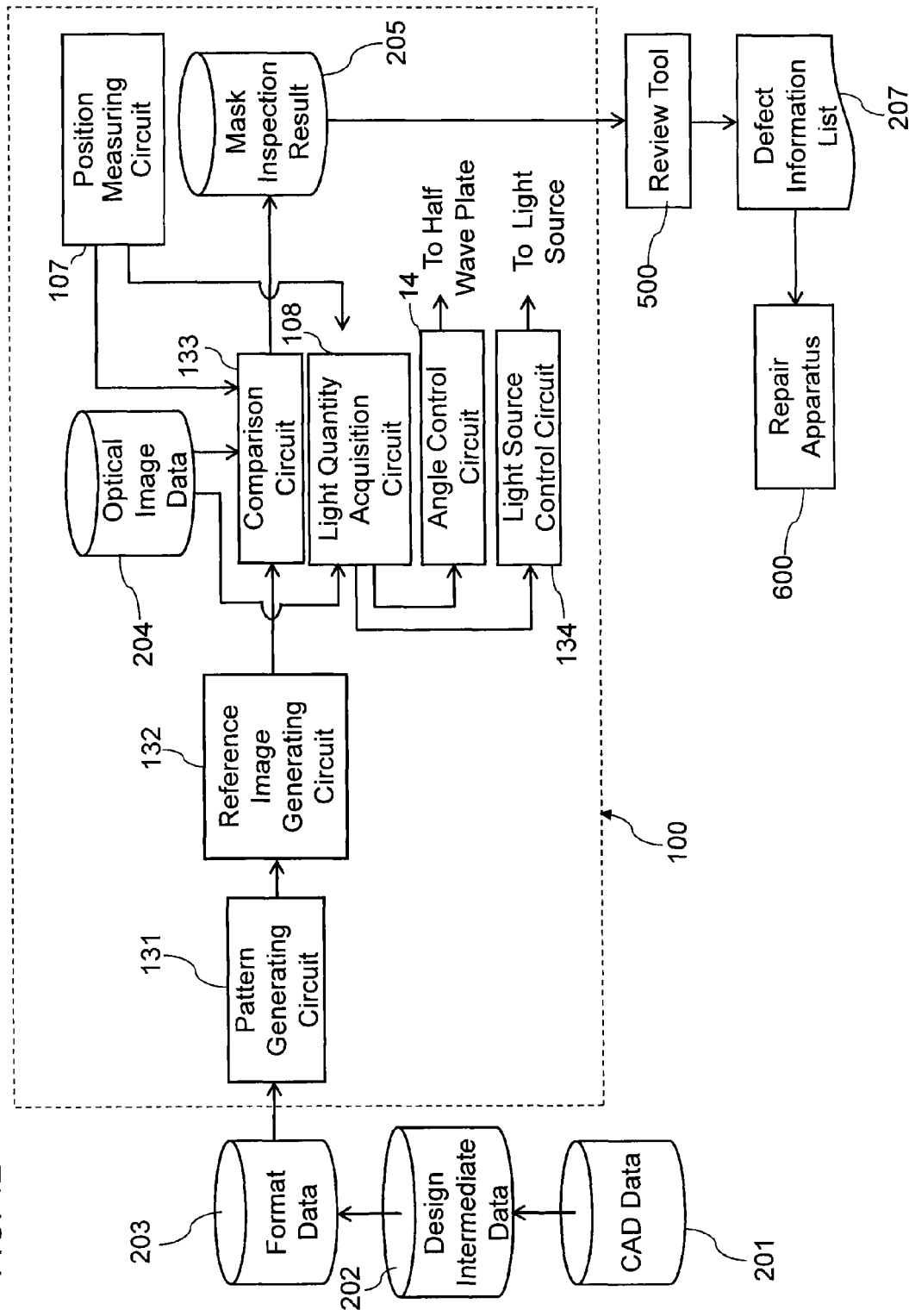
FIG. 12 illustrates data flow according to the first embodiment.

As shown in FIG. 12, CAD data 201 produced by a designer (user) is converted into design intermediate data 202 having a hierarchical format such as OASIS. The design pattern data, which is produced in each layer and formed in the mask, is stored in the design intermediate data 202. At this point, generally the inspection apparatus is configured not to directly read OASIS data. That is, independent format data is used by each manufacturer of an inspection apparatus. For this reason, the OASIS data is input to the inspection apparatus 100 after conversion into format data 203 unique to the inspection apparatus in each layer. In this case, the format data 203 can be set to a data format that is unique to the inspection apparatus 100 or to the data format that is compatible with a drawing apparatus which draws a pattern on a mask.

Figure 1:
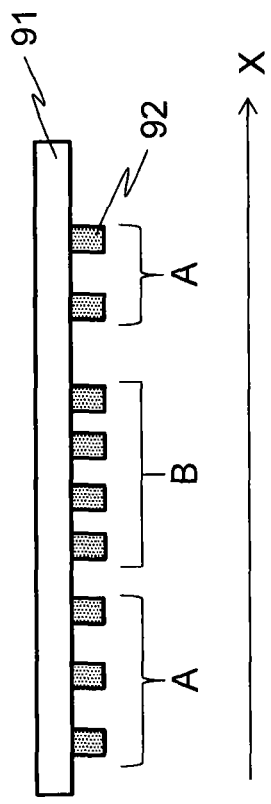
FIG. 1 is a schematic sectional view of the mask.

The format data 203 is input to the magnetic disk drive 109 in FIG. 1. That is, the design pattern data used during the formation of the pattern in the mask 101 is stored in the magnetic disk drive 109.

The figure patterns included in the design pattern, may be a rectangle or a triangle is used as a basic graphic pattern. For example, Graphic data in which the shape, size, and position of each graphic pattern is stored in the magnetic disk drive 109. For example, the graphic data is information such as a coordinate (x, y) from the original position of the graphic pattern, a side length, and a graphic code that is an identifier identifying a graphic pattern type such as a rectangle and a triangle.

A set of graphic patterns existing within a range of several tens of micrometers is generally called a cluster or a cell, and the data is layered using the cluster or cell. In the cluster or cell, a disposition coordinate and a repetitive amount are defined in the case that various graphic patterns are separately disposed or repetitively disposed with a certain distance. The cluster or cell data is disposed in a strip-shaped region called a stripe. The strip-shaped region has a width of several hundred micrometers and a length of about 100 mm that corresponds to a total length in an X-direction or a Y-direction of the sample 1.

The pattern generating circuit 131 reads the input design pattern data from the magnetic disk drive 109 through the control computer 110.

In the pattern generating circuit 131, the design pattern data is converted into image data (bit pattern data). That is, the pattern generating circuit 131 extracts the design pattern data to individual data of each graphic pattern, and interprets the figure pattern code and figure pattern dimension, which indicate the figure pattern shape of the design pattern data. The design pattern data is extracted to binary or multi-level image data as the pattern disposed in a square having a unit of a grid of a predetermined quantization dimension. Then an occupancy rate of the graphic pattern in the design pattern is calculated in each region (square) corresponding to a sensor pixel, and the occupancy rate of the graphic pattern in each pixel becomes a pixel value.

The image data converted by the pattern generating circuit 131 is transmitted to the reference image generating circuit 132, that is, the reference image producing unit, and used to produce a reference image (also referred to as reference data).

The optical image data 204 output from the sensor circuit 106 is transmitted to the comparison circuit 133 together with data indicating a position of the sample 1 on the XY-table 3. The data is output from the position measuring circuit 107. The reference image is also transmitted to the comparison circuit 133.

In the comparison circuit 133, the optical image data 204 and the reference data are compared to each other using a proper comparison determination algorithm. In the configuration of FIG. 11, reflection images are compared to each other. In a configuration in which a transmission optical system is used, transmission images are compared to each other, or a comparison determination algorithm in which reflection and transmission are combined is used. As a result of the comparison, in the case that a difference between the two exceeds a predetermined threshold, the position is determined to be the defect.

In the comparison circuit 133, the reference image corresponding to the (stripe-shaped) optical image data 204 is divided into small rectangular regions of several tens of micrometers called inspection frames. A sensor frame image extracted from the optical image data 204 and a reference frame image extracted from the reference image are input to a comparison unit in the comparison circuit 133. The comparison unit compares the sensor frame image and the reference frame image to each other to detect the defect. Several tens of comparison units are included in the comparison circuit 133 so as to concurrently process multiple inspection frames. Each comparison unit captures the unprocessed frame image when ending the processing of one inspection frame. Therefore, many inspection frames are sequentially processed.

The processing of the comparison unit is specifically performed as follows. The sensor frame image and the reference frame image are aligned with each other. At this point, in order to align edge positions of the pattern or luminance peak positions, the sensor frame image or the reference frame image is shifted in parallel in units of sensor pixels, and the sensor frame image and the reference frame image are aligned up to the sensor pixel or less by prorating luminance values of neighboring pixels. After the alignment, a level difference between the sensor frame image and the reference frame image is evaluated in each pixel, and derivative values of the pixels in a pattern edge direction are compared to each other, whereby the defect is detected according to the proper comparison algorithm. Hereinafter, occasionally the comparison of the sensor frame image and the reference frame image is simply referred to as comparison of the optical image and the reference image.

In the present embodiment, the optical image data 204 is also transmitted to the light quantity acquisition circuit 108. The position measuring circuit 107 transmits the data indicating the position of the sample 1 on the XY-table 3 to the light quantity acquisition circuit 108.

In the light quantity acquisition circuit 108, the optical image data 204 is expressed by a gradation value in each pixel. For example, one of values from a 0 gradation level to a 255 gradation level is provided to each pixel using a gray scale having a 256-level gradation value. The light quantity values of the first and second sensors 2008 and 2009 are obtained from the gradation values of the images captured with the first and second sensors 2008 and 2009, and the light quantity ratio (1/A) of the second sensor 2009 to the first sensor 2008 is obtained from the light quantity values. Then, the relationship between the angle of the half-wave plate 2002 and the light quantity ratio (1/A) is obtained, and the angle θ is obtained from the relationship such that the light quantity ratio of the second sensor 2009 to the first sensor 2008 becomes A:1.

The information on the angle θ obtained by the light quantity acquisition circuit 108 is transmitted to the angle control circuit 14. The angle control circuit 14 controls the angle of the half-wave plate 2002. Specifically, the angle control circuit 14 controls a rotating mechanism 2010 provided in the half-wave plate 2002 such that the light quantity ratio of the second sensor 2009 to the first sensor 2008 becomes A:1, thereby adjusting the angle of the half-wave plate 2002.

The pattern of the sample 1 is imaged with the first and second sensors 2008 and 2009 after the angle of the half-wave plate 2002 is adjusted. The light quantity values of the first and second sensors 2008 and 2009 are obtained by the light quantity acquisition circuit 108. In the case that each of the light quantity values is much larger or smaller than the target value, the light quantity acquisition circuit 108 transmits a signal to the light source control circuit 134.

According to an instruction from the light quantity acquisition circuit 108, the light source control circuit 134 adjusts the light quantity introduced to the optical system from the light source 2001 such that each of the light quantity values of the first and second sensors 2008 and 2009 becomes the target value. Therefore, the first sensor 2008 can perform the imaging with the light quantity value suitable for the dense pattern area, and the second sensor 2009 can perform the imaging with the light quantity value suitable for the coarse pattern area.

Although the components necessary in the first embodiment are illustrated in FIG. 11, another well-known component necessary to inspect the sample 1 may be included. The die-to-database inspection method is described in the first embodiment by way of example. On the other hand, in the die-to-die inspection method, one of the optical images of the same patterns located in different regions in the surface of the sample 1 is dealt with as the standard image.

An example of a method for inspecting the sample 1 with the inspection apparatus 100 of FIG. 11 will be described below.

(Process of Adjusting Angle of Half-Wave Plate and Light Quantity of Light Source)

The angle of the half-wave plate 2002 is adjusted such that the light quantity value of the first sensor 2008 is suitable for the dense pattern area and such that the light quantity value of the second sensor 2009 is suitable for the coarse pattern area. The light quantity of the light source 2001 is also adjusted. The adjustment is performed as follows.

The pattern of the sample 1 is imaged with the first and second sensors 2008 and 2009. Although the whole pattern of the sample 1 is not necessarily imaged, at least the dense pattern area and the coarse pattern area are imaged. Not the pattern of the sample 1 that is the inspection target but the pattern of the mask that is a previously-fixed standard may be used. A specific process of acquiring the optical image is described later.

The light quantity values of the first and second sensors 2008 and 2009 are obtained from gradation values of the images captured with the first and second sensors 2008 and 2009. The light quantity ratio (1/A) of the second sensor 2009 to the first sensor 2008 is obtained from the light quantity values. Then the relationship between the angle of the half-wave plate 2002 and the light quantity ratio (1/A) is obtained, and the angle θ is obtained from the relationship such that the light quantity ratio of the second sensor 2009 to the first sensor 2008 becomes A:1.

The information on the angle θ obtained by the light quantity acquisition circuit 108 is transmitted to the angle control circuit 14. The angle control circuit 14 controls the angle of the half-wave plate 2002. That is, the angle control circuit 14 controls the rotating mechanism 2010 provided in the half-wave plate 2002 such that the light quantity ratio of the second sensor 2009 to the first sensor 2008 becomes A:1, thereby adjusting the angle of the half-wave plate 2002.

The pattern of the sample 1 is imaged with the first and second sensors 2008 and 2009 again after the angle of the half-wave plate 2002 is adjusted. The light quantity values of the first and second sensors 2008 and 2009 are obtained by the light quantity acquisition circuit 108. The light quantity of the light source is adjusted in the case that each of the light quantity values is much larger or smaller than the target value.

Specifically, the light quantity acquisition circuit 108 transmits the signal to the light source control circuit 134. According to the instruction from the light quantity acquisition circuit 108, the light source control circuit 134 adjusts the light quantity introduced to the optical system from the light source 2001 such that each of the light quantity values of the first and second sensors 2008 and 2009 becomes the target value. Therefore, the first sensor 2008 can perform the imaging with the light quantity value suitable for the dense pattern area, and the second sensor 2009 can perform the imaging with the light quantity value suitable for the coarse pattern area.

(Optical Image Acquisition Process)

As described above, by adjusting the angle of the half-wave plate 2002 and the light quantity of the light source 2001, the light quantity value of the first sensor 2008 is suitable for the dense pattern area, and the light quantity value of the second sensor 2009 is suitable for the coarse pattern area. At this point, the optical image for the inspection is obtained.

Figure 13:
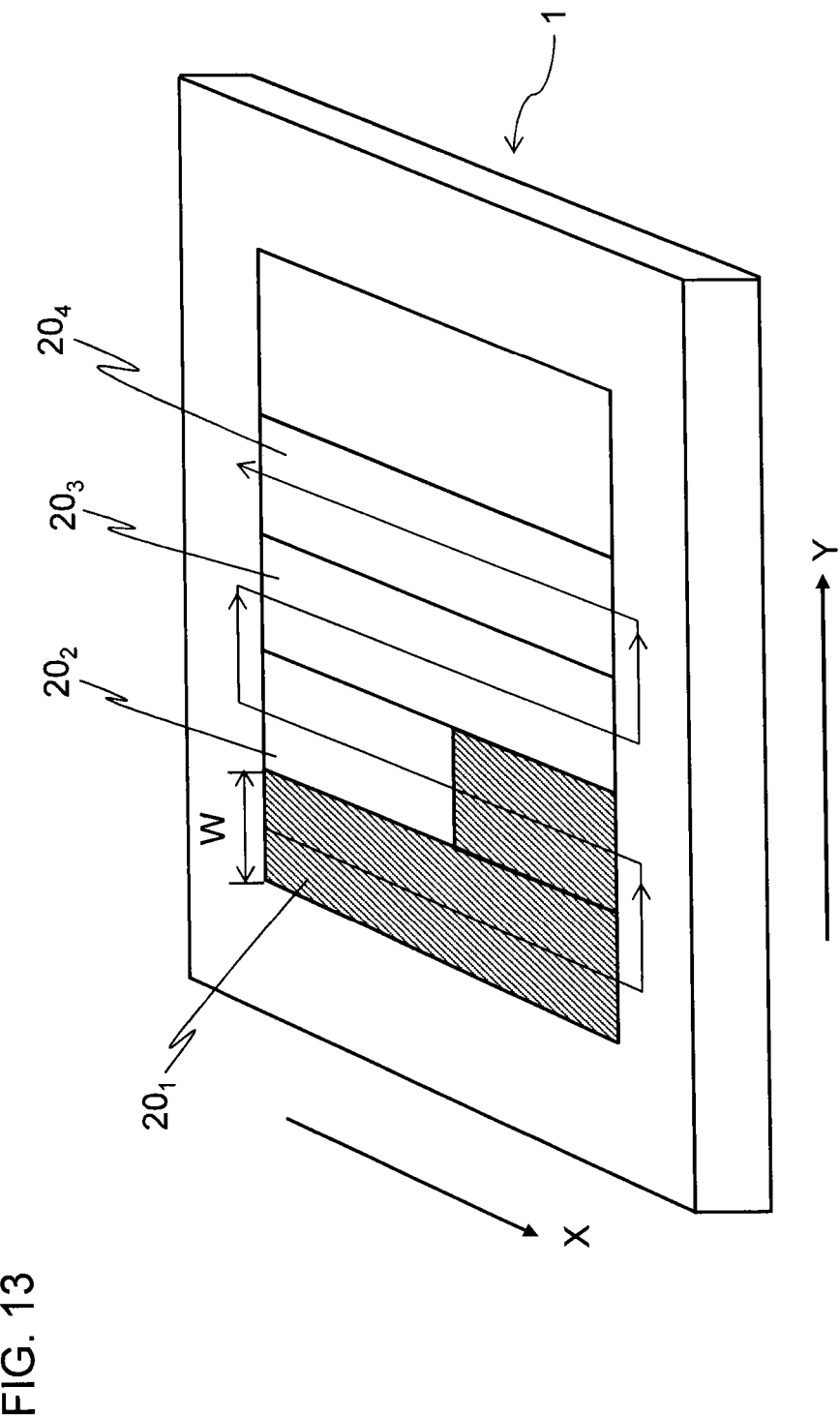
FIG. 13 illustrates an acquisition procedure of an optical image of a sample.

The configuration unit A of FIG. 11 acquires the optical image of the sample 1. FIG. 13 illustrates an acquisition procedure of the optical image of the sample 1. As described above, the optical image corresponds to the optical image data 204 of FIG. 12.

In FIG. 13, it is assumed that the sample 1 is positioned on the XY-table 3 in FIG. 11. The inspection region in the sample 1 is virtually divided into the strip-shaped multiple inspection regions, namely, stripes $20_1$, $20_2$, $20_3$, $20_4$, . . . as illustrated in FIG. 13. For example, each stripe is a region having the width of several hundred micrometers and the length of about 100 mm corresponding to the total length in the X-direction or Y-direction of the sample 1.

The optical image is acquired in each stripe by the first sensor 2008 and the second sensor 2009 of FIG. 11. That is, in acquiring the optical image in FIG. 13, the operation of the XY-table 3 is controlled such that the each stripe $20_1$, $20_2$, $20_3$, $20_4$, . . . is continuously scanned. Specifically, the optical image of the sample 1 is acquired while the XY-table 3 moved in the -X-direction of FIG. 13. The image having a scan width W as shown in FIG. 13 is continuously input to the first sensor 2008 and the second sensor 2009. That is, the image of the second stripe $20_2$ is acquired after the image of the first stripe $20_1$ is acquired. In this case, after the XY-table 3 moves in the -Y-direction in a stepwise manner, the optical image is acquired while the XY-table 3 moves in the direction (X-direction) opposite to the direction (-X-direction) in which the image of the first stripe $20_1$ is acquired, and the image having the scan width W is continuously input to the first sensor 2008 and the second sensor 2009. In the case that the image of the third stripe $20_3$ is acquired, after moving in the -Y-direction in the stepwise manner, the XY-table 3 moves in the direction opposite to the direction (X-direction) in which the image of the second stripe $20_2$ is acquired, namely, the direction (-X-direction) in which the image of the first stripe $20_1$ is acquired. An arrow in FIG. 13 indicates the optical image acquiring direction and sequence, and a hatched portion indicates the region where the optical image is already acquired.

The first sensor 2008 and the second sensor 2009 performs the photoelectric conversion to the pattern image formed on the first sensor 2008 and the second sensor 2009 in FIG. 11, and the sensor circuit 106 performs the A/D (analog-digital) conversion to the pattern image. Then the optical image is transmitted from the sensor circuit 106 to the comparison circuit 133.

The A/D-converted sensor data is input to a digital amplifier (not illustrated) that can adjust an offset and a gain in each pixel. The gain for each pixel of the digital amplifier is fixed in a calibration process. For example, in the calibration process for transmitted light, a black level is fixed while the image of a light-shielding region in the sample 1, sufficiently wide with respect to an area in which the image is captured by the sensor, is captured. Then a white level is fixed while the image of a transmitted light region in the sample 1, sufficiently wide with respect to an area in which the image is captured by the sensor, is captured. At this point, in consideration of a fluctuation in light quantity during the inspection, the offset and the gain are adjusted in each pixel such that amplitudes of the white level and black level are distributed in a range of 10 to 240 corresponding to about 4% to about 94% of 8-bit gradation data.

(Reference Image Generating Process)
(1) Storage Process

In the case of inspection by the die-to-database comparison method, the reference image generated from the design pattern data becomes a reference of the defect determination. In the inspection apparatus 100, the design pattern data used to form the pattern in the sample 1 is stored in the magnetic disk drive 109.

(2) Pattern Generating Process

In the pattern generating process, the pattern generating circuit 131 of FIG. 11 reads the design pattern data from the magnetic disk drive 109 through the control computer 110, and converts the read design pattern data of the sample 1 into the binary or multi-value image data (design image data). The image data is transmitted to the reference image generating circuit 132.

(3) Filtering Process

In the filtering process, the reference image generating circuit 132 of FIG. 11 performs the proper filtering to the design pattern data, that is, the graphic image data. The reason is as follows.

In the production process because roundness of the corner and a finished dimension of the line width is adjusted, the pattern in the sample 1 is not strictly matched with the design pattern. The optical image data 204, that is, the optical image obtained from the sensor circuit 106 in FIG. 11 is faint due to a resolution characteristic of the optical system or an aperture effect of the sensors, in other words, the state in which a spatial lowpass filter functions. Therefore, the mask that is the inspection target is observed in advance of the inspection, a filter coefficient imitating the production process or a change of an optical system of the inspection apparatus is determined to subject the design pattern data to a two-dimensional digital filter. Thus, the processing of imitating the optical image is performed to the reference image.

The learning process of the filter coefficient may be performed using the pattern of the mask that is the reference fixed in the production process or a part of the pattern of the sample 1 that is the inspection target. In the latter case, the filter coefficient is acquired in consideration of the pattern line width of the region used in the learning process or a finished degree of the roundness of the corner, and reflected in a defect determination criterion of the whole mask.

In the case that the mask that is the inspection target is used, advantageously the learning process of the filter coefficient can be performed without removing influences such as a variation of production lot and a fluctuation in condition of the inspection apparatus. However, when the dimension fluctuates in the surface of the mask, the filter coefficient becomes optimum with respect to the position used in the learning process, but the filter coefficient does not necessarily become optimum with respect to other positions, which results in a pseudo defect. Therefore, preferably the learning process is performed around the center of surface of the mask that is hardly influenced by the fluctuation in dimension. Alternatively, the learning process is performed at multiple positions in the surface of the mask, and the average value of the obtained multiple filter coefficients may be used.

(Comparison Process)

Because the angle of the half-wave plate 2002 and the light quantity of the light source 2001 are adjusted, the first sensor 2008 becomes the light quantity value suitable for the dense pattern area, and the second sensor 2009 becomes the light quantity value suitable for the coarse pattern area. Therefore, the image captured with the first sensor 2008 is used to inspect the dense pattern area, and the image captured with the second sensor 2009 is used to inspect the coarse pattern area.

As illustrated in FIG. 12, the optical image data 204 obtained through the optical image acquisition process is transmitted to the comparison circuit 133. At this point, the optical image data 204 includes the data imaged by the first sensor 2008 and the data imaged by the second sensor 2009. The reference image generating circuit 132 transmits the reference data to the comparison circuit 133.

In the comparison circuit 133, the optical image data 204 and the reference data are compared to each other by the die-to-database method. Specifically, the imaged stripe data is cut out in units of inspection frames, and is compared to the data that is a defect criterion in each inspection frame using a comparison determination algorithm. At this point, for the dense pattern area of the sample 1, the optical image data 204 imaged with the first sensor 2008 is compared to the reference data. On the other hand, for the coarse pattern area of the sample 1, the optical image data 204 imaged with the second sensor 2009 is compared to the reference data.

As a result of the comparison, the place where a difference between the optical image data 204 and the reference data exceeds a predetermined threshold is determined to be the defect. The information on the defect is stored as a mask inspection result 205. For example, the control computer 110 stores a coordinate of the defect and the optical image warranting the defect determination as the mask inspection result 205 in the magnetic disk device 109.

More specifically the defect determination can be made by the following two methods. One of the methods is the method for determining that the inspection target is the defect in the case that the difference exceeding a predetermined threshold is recognized between the position of a contour in the reference image and the position of a contour in the optical image. The other method is the method for determining that the inspection target is the defect in the case that the ratio of the pattern line width in the reference image and the pattern line width in the optical image exceeds a predetermined threshold. In this method, the ratio of the inter-pattern distance in the reference image and the inter-pattern distance in the optical image may be used.

Figure 2:
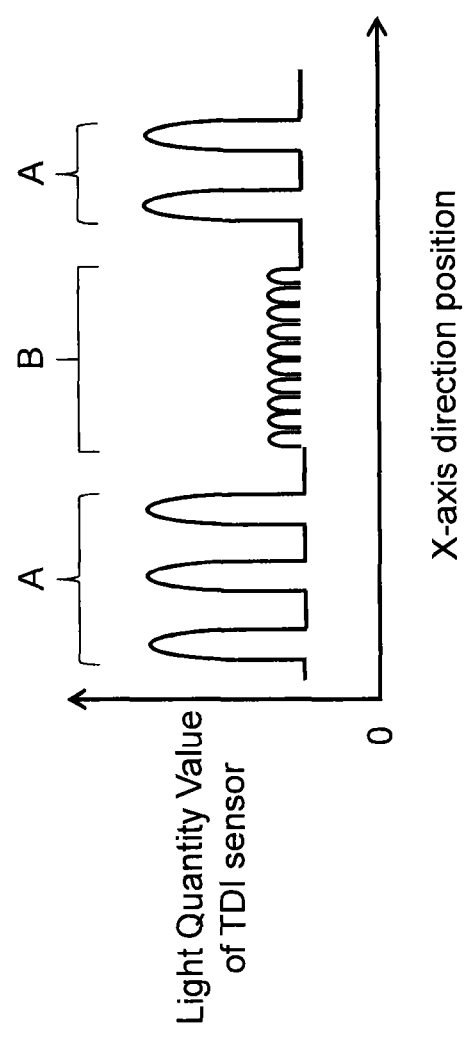
FIG. 2 illustrates a light quantity value of light incident to a TDI sensor when the pattern of FIG. 1 is imaged along an X-axis direction.

After that, the mask inspection result 205 is transmitted to a review tool 500 as shown in FIG. 12. A review process is an operation in which the operator determines whether the detected defect will become a practical problem. For example, the operator visually determines whether the defect needs to be corrected by comparing the reference image, that is, the basis for the defect determination, to the optical image including the defect. The defect information determined through the review process is also stored in the magnetic disk drive 109 of FIG. 11. As illustrated in FIG. 2, when the defect to be corrected is confirmed by the review tool 500, the sample 1 is transmitted to a repair apparatus 600, that is, the external device of the inspection apparatus 100 together with a defect information list 207. Because a correction method depends on whether the defect is projected or recessed, a defect type including the distinction between the projection and the recess and the defect coordinate are added to the defect information list 207.

As described above, in the first embodiment, the high-resolution optical image is obtained because the sample that is the inspection target is illuminated with the linearly-polarized light. In the first embodiment, by adjusting the angle of the half-wave plate and the light quantity of the light source, the light quantity value of the first sensor is suitable to obtain the image of the dense pattern area, and the light quantity value of the second sensor is suitable to obtain the image of the coarse pattern area. The image captured with the first sensor is used to inspect the dense pattern area, and the image captured with the second sensor is used to inspect the coarse pattern area. Therefore, the inspection apparatus and the inspection method for being able to accurately inspect both the dense pattern area and the coarse pattern area are provided.

Second Embodiment

In the first embodiment, the inspection target is illuminated with the linearly-polarized light. Alternatively, the inspection target may be illuminated with circularly-polarized light. When the inspection target is illuminated with the linearly-polarized light, directionality is generated in a resolution characteristic, while the high-resolution optical image is obtained. The directionality can be eliminated by illuminating the inspection target with the circularly-polarized light.

Figure 14:
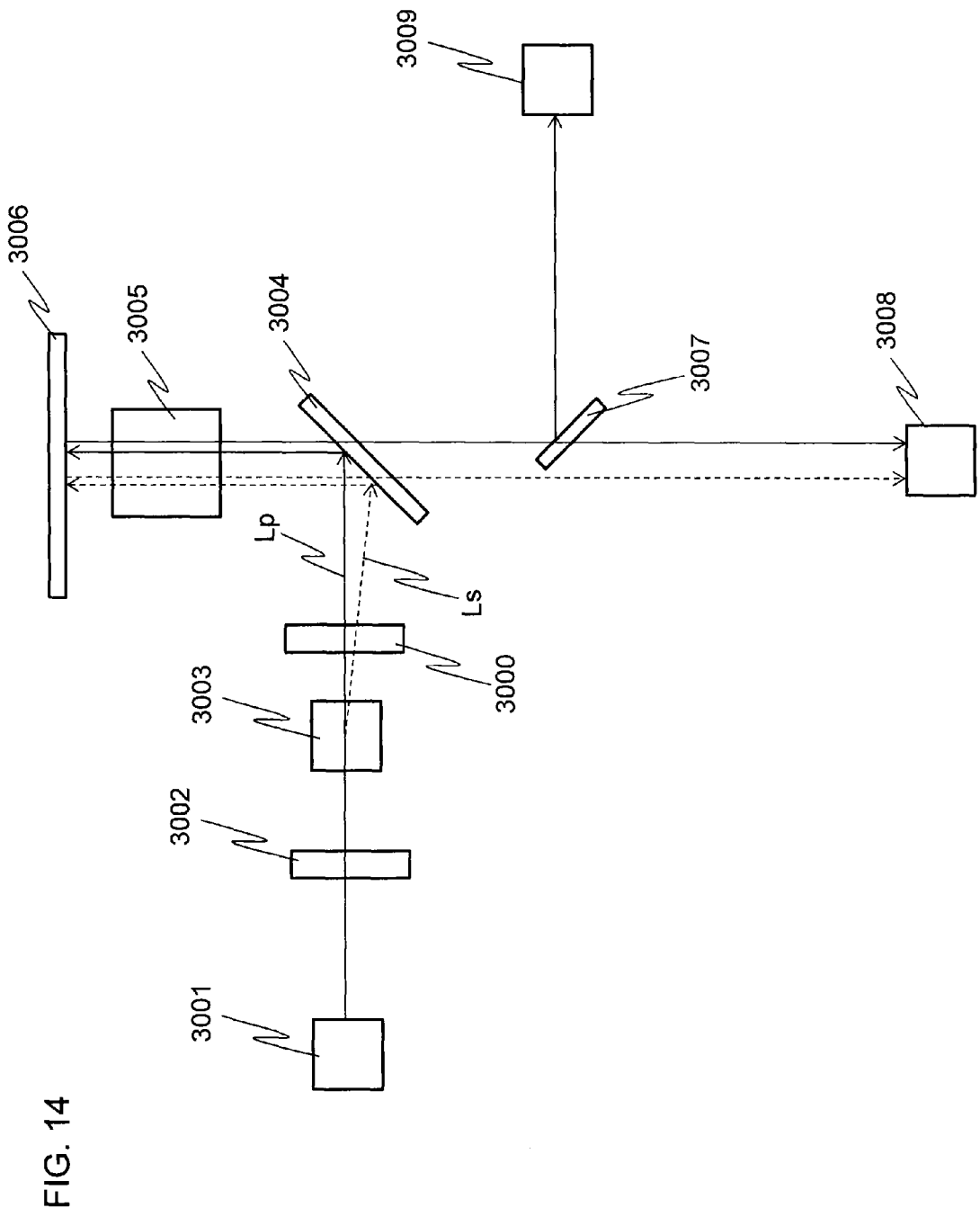
FIG. 14 is a schematic diagram illustrating a configuration of an optical system in an inspection apparatus according to a second embodiment.

FIG. 14 is a schematic diagram illustrating a configuration of an optical system in an inspection apparatus according to a second embodiment. The inspection apparatus of the second embodiment has the same configuration as that in FIG. 11 except that the optical system of the first embodiment in FIG. 5 is replaced with the optical system in FIG. 14.

The illumination optical system will be described below.

In FIG. 14, the laser beam source that emits the linearly-polarized light can be used as a light source 3001. The light emitted from the light source 3001 is incident to a Rochon prism 3003 that is of the branching element while the phase of the light is rotated by 90° using a half-wave plate 3002. At this point, the angle of the half-wave plate 3002 is set such that the amount of p-polarized light (Lp) incident to the Rochon prism 3003 is equal to the amount of s-polarized light (Ls) incident to the Rochon prism 3003.

Although the Rochon prism 3003 transmits the p-polarized light component (Lp) straight, the Rochon prism 3003 transmits the s-polarized light component (Ls) while displacing the s-polarized light component from the original optical axis. The polarizing prism except the Rochon prism 3003 may be used as long as the polarizing prism branches the polarized light components orthogonal to each other into two.

The light transmitted through the Rochon prism 3003 is incident to a quarter-wave plate 3000. The quarter-wave plate 3000 changes the linearly-polarized light to the circularly-polarized light. After the p-polarized light (Lp) and the s-polarized light (Ls) are reflected by a half mirror 3004, a mask 3006 that is the inspection target is illuminated with the p-polarized light and the s-polarized light through an objective lens 3005.

The mask 3006 may have the configuration in FIG. 1. In the present invention, the EUV mask in FIG. 3 is particularly suitable for the mask 3006. A predetermined pattern such as the line and space pattern is provided in the mask 3006. In the case that the mask 3006 is the configuration in FIG. 3, the absorbing layer (the film 95) on the reflecting layer (the multilayer film 94) is the patterned layer. The density of the pattern provided in the mask 3006 is not constant. Such the region as the memory mat portion of the semiconductor chip, where the pattern density is high, and such the region as the peripheral circuit portion of the semiconductor chip, where the pattern density is low, are mixed in the pattern.

The light reflected by the mask 3006 is incident to the imaging optical system through the objective lens 3005 and the half mirror 3004.

In FIG. 14, two sensors 3008 and 3009 that are of the imaging element are provided in the imaging optical system. For example, the TDI sensor may be used as the sensor.

The s-polarized light (Ls) reflected by the mask 3006 is incident to the first sensor 3008. On the other hand, the p-polarized light (Lp) reflected by the mask 3006 is incident to the second sensor 3009 while the optical path of the p-polarized light is changed by the half mirror 3007.

The first and second sensors 3008 and 3009 image the same mask 3006. At this point, the pattern of the absorbing layer has the dense pattern area and the coarse pattern area as illustrated in FIG. 3. In the second embodiment, the light quantity values of the first and second sensors 3008 and 3009 are adjusted according to the method of the first embodiment in FIG. 6. Specifically, the light quantity of the light source 3001 and the angle of the half-wave plate 3002 are adjusted such that the first sensor 3008 becomes the light quantity value suitable for the dense pattern area and such that the second sensor 3009 becomes the light quantity value suitable for the coarse pattern area.

That is, the angle of the half-wave plate 3002 is set such that the amount of p-polarized light (Lp) incident to the Rochon prism 3003 is equal to the amount of s-polarized light (Ls) incident to the Rochon prism 3003. Then the pattern of the mask 3006 is imaged with the first and second sensors 3008 and 3009. Although the whole pattern of the mask 3006 is not necessarily imaged, at least the dense pattern area and the coarse pattern area are imaged. Not the pattern of the mask 3006 but the pattern of the mask that is a previously-fixed standard may be used.

(1) Whether the light quantity value of the first sensor 3008 reaches the saturation, or (2) whether the light quantity value of the second sensor 3009 is lacking, namely, whether the light quantity value of the second sensor 3009 does not reach the value enough to obtain the sufficient contrast is determined irrespective of the dense or coarse pattern. When one of the conditions (1) and (2) is satisfied, the light quantity introduced to the optical system from the light source 3001 is adjusted. Then, the light quantity of the light source 3001 is adjusted until both the conditions (1) and (2) are not satisfied.

Then the light quantity ratio (1/A) of the second sensor 3009 to the first sensor 3008 is obtained from the dense pattern area imaged with the first sensor 3008 and the coarse pattern area imaged with the second sensor 3009. Then the relationship between the angle of the half-wave plate 3002 and the light quantity ratio (1/A) is obtained, and the angle of the half-wave plate 3002 is adjusted from the relationship such that the light quantity ratio of the second sensor 3009 to the first sensor 3008 becomes A:1. The light quantity introduced to the optical system from the light source 3001 is adjusted in the case that each of the light quantity values of the first and second sensors 3008 and 3009 is much larger or smaller than the target value. Then, the determination is made again, and the light quantity of the light source 3001 is adjusted until each light quantity value reaches the target value.

Thus, the first sensor 3008 can image the pattern with the light quantity value suitable for the dense pattern area, and the second sensor 3009 can image the pattern with the light quantity value suitable for the coarse pattern area.

As described above, the optical system in FIG. 14 can be applied to the inspection apparatus in FIG. 11. In this case, the illumination optical system in FIG. 14 may be replaced with a transmission type illumination optical system. In the configuration in FIG. 14, the light reflected by the mask 3006 is introduced to the first and second sensors 3008 and 3009. Alternatively, the mask 3006 is illuminated with the light from above, and the light transmitted through the mask 3006 may be introduced to the sensors. A combination of the both can simultaneously obtain the optical images of the transmitted light and the reflected light.

Another well-known component necessary to inspect the mask 3006 may be included in the inspection apparatus of the second embodiment. The die-to-database inspection method is described in the second embodiment by way of example. On the other hand, in the die-to-die inspection method, one of the optical images of the same patterns located in different regions in the surface of the mask 3006 is dealt with as the standard image.

The inspection method in which the inspection apparatus is used can be performed as follows. The inspection method will be described below with reference to FIGS. 11 and 14.

(Process of Adjusting Angle of Half-Wave Plate and Light Quantity of Light Source)

The angle of the half-wave plate 3002 is adjusted such that the light quantity value of the first sensor 3008 in FIG. 14 is suitable for the dense pattern area and such that the light quantity value of the second sensor 3009 is suitable for the coarse pattern area. The light quantity of the light source 3001 is also adjusted. The adjustment is performed as follows.

The pattern of the mask 3006 is imaged with the first and second sensors 3008 and 3009. Although the whole pattern of the sample 1 is not necessarily imaged, at least the dense pattern area and the coarse pattern area are imaged. Not the pattern of the sample 1 that is the inspection target but the pattern of the mask that is the previously-fixed standard may be used. A specific process of acquiring the optical image is described later.

The light quantity values of the first and second sensors 3008 and 3009 are obtained from the gradation values of the images captured with the first and second sensors 3008 and 3009. The light quantity ratio (1/A) of the second sensor 3009 to the first sensor 3008 is obtained from the light quantity values. Then the relationship between the angle of the half-wave plate 3002 and the light quantity ratio (1/A) is obtained, and the angle θ is obtained from the relationship such that the light quantity ratio of the second sensor 3009 to the first sensor 3008 becomes A:1. Then the angle of the half-wave plate 3002 is adjusted to the angle θ.

The pattern of the mask 3006 is imaged with the first and second sensors 3008 and 3009 again. The light quantity of the light source 3001 is adjusted in the case that each of the light quantity values of the first and second sensors 3008 and 3009 is much larger or smaller than the target value. Therefore, the first sensor 3008 can perform the imaging with the light quantity value suitable for the dense pattern area, and the second sensor 3009 can perform the imaging with the light quantity value suitable for the coarse pattern area.

(Optical Image Acquisition Process)

As described above, by adjusting the angle of the half-wave plate 3002 and the light quantity of the light source 3001, the light quantity value of the first sensor 3008 is suitable for the dense pattern area, and the light quantity value of the second sensor 3009 is suitable for the coarse pattern area. At this point, the optical image for the inspection is obtained. The optical image for the inspection is obtained in the procedure similar to that of the first embodiment in FIG. 13. In the second embodiment, because the mask 3006 is illuminated with the circularly-polarized light, the optical image having the resolution characteristic is obtained without the directionality.

After photoelectric conversion, the sensor circuit 106 in FIG. 11 performs A/D (Analog-to-Digital) conversion to the patterns imaged with the first and second sensors 3008 and 3009. Then the optical image is transmitted to the comparison circuit 133 from the sensor circuit 106.

(Reference Image Generation Process)

(1) Storage Process

In the case of inspection by the die-to-database comparison method, the reference image generated from the design pattern data becomes a reference of the defect determination. The design pattern data used to form the pattern in the mask 3006 is stored in the magnetic disk drive 109 of FIG. 11.

(2) Pattern Generating Process

In the pattern generating process, the pattern generating circuit 131 of FIG. 11 reads the design pattern data from the magnetic disk drive 109 through the control computer 110, and converts the read design pattern data into the binary or multi-value image data (design image data). The image data is transmitted to the reference image generating circuit 132.

(3) Filtering Process

In the filtering process, the reference image generating circuit 132 of FIG. 11 performs the proper filtering to the design pattern data, that is, the graphic image data. The learning process of the filter coefficient may be performed using the pattern of the mask that is the reference fixed in the production process or a part of the pattern of the mask 3006 that is the inspection target. In the latter case, the filter coefficient is acquired in consideration of the pattern line width of the region used in the learning process or a finished degree of the roundness of the corner, and reflected in a defect determination criterion of the whole mask 3006. Therefore, preferably the learning process is performed around the center of surface of the mask 3006 that is hardly influenced by the fluctuation in dimension. Alternatively, the learning process is performed at multiple positions in the surface of the mask 3006, and the average value of the obtained multiple filter coefficients may be used.

(Comparison Process)

Because the light quantity of the light source 3001 and the angle of the half-wave plate 3002 are adjusted, the first sensor 3008 becomes the light quantity value suitable for the dense pattern area, and the second sensor 3009 becomes the light quantity value suitable for the coarse pattern area. Therefore, the image captured with the first sensor 3008 is used to inspect the dense pattern area, and the image captured with the second sensor 3009 is used to inspect the coarse pattern area.

In the comparison circuit 133 in FIG. 11, the optical image and the reference image are compared to each other by the die-to-database method. At this point, for the dense pattern area of the mask 3006, the optical image captured with the first sensor 3008 is compared to the reference data. On the other hand, for the coarse pattern area of the mask 3006, the optical image captured with the second sensor 3009 is compared to the reference data.

As a result of the comparison, the place where a difference between optical image and the reference image exceeds a predetermined threshold is determined to be the defect. The information regarding the defect is stored as a mask inspection result. For example, the control computer 110 of FIG. 11 stores the defect coordinates and the optical image, which is the basis of the defect determination, as a mask inspection result in the magnetic disk drive 109.

After that, the mask inspection result is transmitted to a review tool and the operator determines whether the detected defect will become a practical problem. The defect information determined through the review process is also stored in the magnetic disk drive 109 of FIG. 11. When the defect to be corrected is confirmed by the review tool, the mask 3006 is transmitted to a repair apparatus, that is, the external device of the inspection apparatus together with a defect information list.

In the second embodiment, because the sample that is of the inspection target is illuminated with the circularly-polarized light, the optical image having the resolution characteristic is obtained without the directionality. In the second embodiment, similarly to the first embodiment, the angle of the half-wave plate and the light quantity of the light source are adjusted such that the light quantity value of the first sensor is suitable for obtaining an image of the dense pattern area, and such that the light quantity value of the second sensor is suitable for obtaining an image of the coarse pattern area. The image captured with the first sensor is used to inspect the dense pattern area, and the image captured with the second sensor is used to inspect the coarse pattern area. Therefore, the inspection apparatus and the inspection method for being able to accurately inspect both the dense pattern area and the coarse pattern area are provided.

Third Embodiment

In the first and second embodiments, the polarizing prism is arranged in the illumination optical system to branch the light emitted from the light source into two. In a third embodiment, the light is branched by the imaging optical system by way of example.

Figure 15:
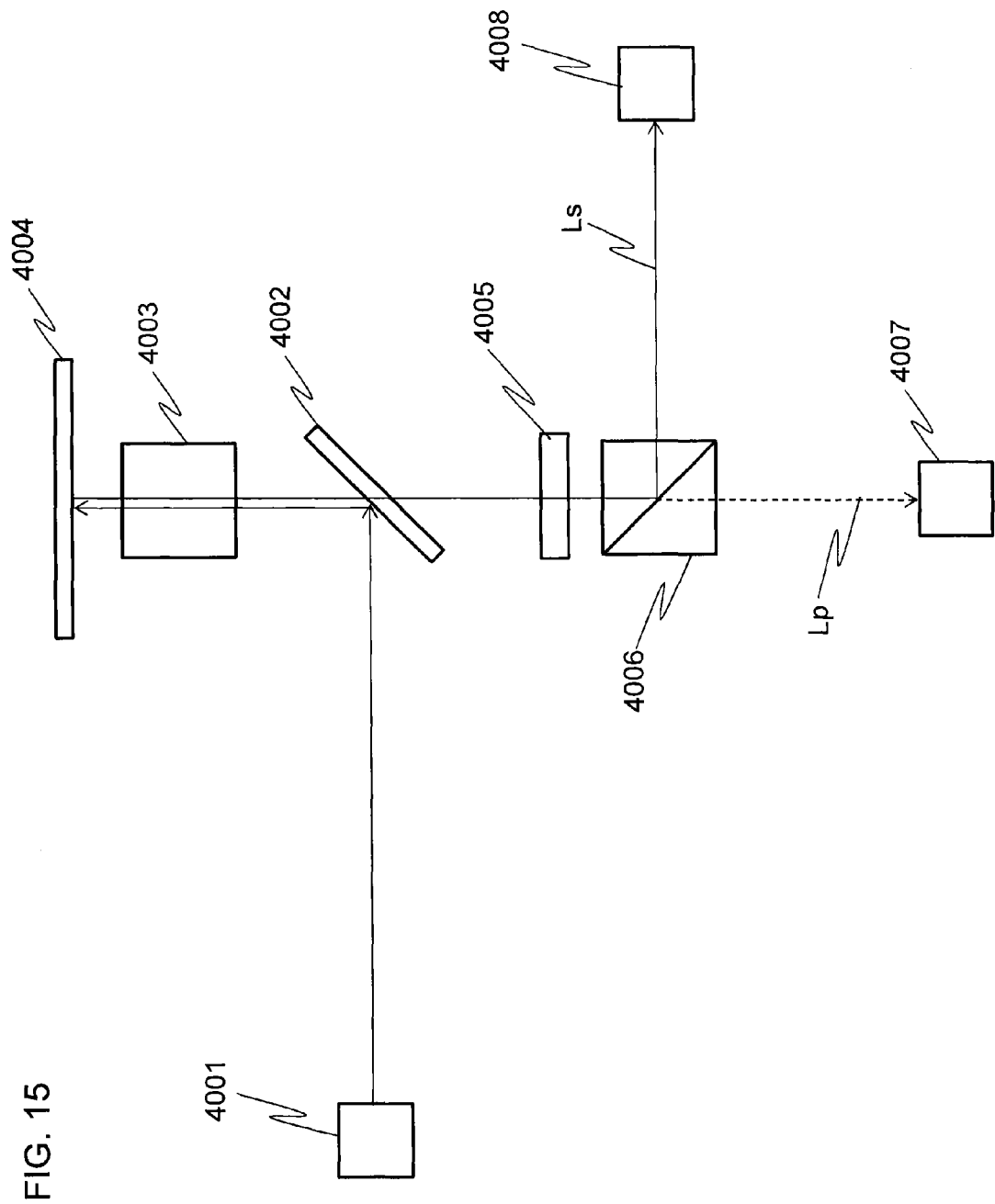
FIG. 15 is a schematic diagram illustrating a configuration of an optical system in an inspection apparatus according to a third embodiment.

FIG. 15 is a schematic diagram illustrating a configuration of an optical system of an inspection apparatus according to the present embodiment.

First the illumination optical system will be described. The laser beam source can be used as a light source 4001 in FIG. 15. After the light emitted from the light source 4001 is reflected by a half mirror 4002, a mask 4004 that is the inspection target is illuminated with the light through an objective lens 4003. The light reflected by the mask 4004 is incident to the imaging optical system through the objective lens 4003 and the half mirror 4002.

In FIG. 15, a half-wave plate 4005, a polarization beamsplitter 4006 that is of the branching element, and two sensors 4007 and 4008 that are of the imaging element are provided in the imaging optical system. For example, the TDI sensor can be used as the sensor.

After the phase of the linearly-polarized light emitted from the light source 4001 is rotated by 90° using the half-wave plate 4005, the linearly-polarized light is incident to the polarization beamsplitter 4006. At this point, the angle of a half-wave plate 4005 is set such that the quantity of p-polarized light (Lp) incident to the polarization beamsplitter 4006 is equal to the quantity of s-polarized light (Ls) incident to the polarization beamsplitter 4006. The polarization beamsplitter 4006 transmits p-polarized light component (Lp) while reflecting the s-polarized light component (Ls). A polarizing filter except the polarization beamsplitter 4006 may be used as the branching element of the third embodiment as long as the polarizing filter separates the incident light with the polarized light components.

The p-polarized light (Lp) reflected by the mask 4004 is incident to the first sensor 4007 through the polarization beamsplitter 4006. On the other hand, the s-polarized light (Ls) reflected by the mask 4004 is reflected by the polarization beamsplitter 4006, and is incident to the second sensor 4008.

The EUV mask in FIG. 3 can be used as the mask 4004. The mask is not limited to the EUV mask. For example, the mask may have the configuration in FIG. 1, or the mask may be the wafer.

In the case that the mask 4004 is the EUV mask, the reflecting layer is formed on the glass substrate, and the patterned absorbing layer is formed on the reflecting layer. For example, the multilayer film that is made of molybdenum and silicon while constructed with a predetermined number of layers is stacked in the reflecting layer. The absorbing layer is made of a material having the high absorption coefficient with respect to the EUV light. The buffer film may be provided between the reflecting layer and the absorbing layer.

The buffer film can reduce the damage to the reflecting layer in patterning the absorbing layer or correcting the defect.

The first and second sensors 4007 and 4008 in FIG. 15 image the same mask 4004. At this point, the pattern of the mask 4004, for example, the pattern of the absorbing layer has the dense pattern area and the coarse pattern area as illustrated in FIG. 3. In the third embodiment, according to the following method, the first sensor 4007 images the pattern with the light quantity value suitable for the dense pattern area, and the second sensor 4008 images the pattern with the light quantity value suitable for the coarse pattern area. Specifically, the imaging is performed with the first and second sensors 4007 and 4008 by adjusting the light quantity of the light source 4001 and the angle of the half-wave plate 4005.

Figure 16:
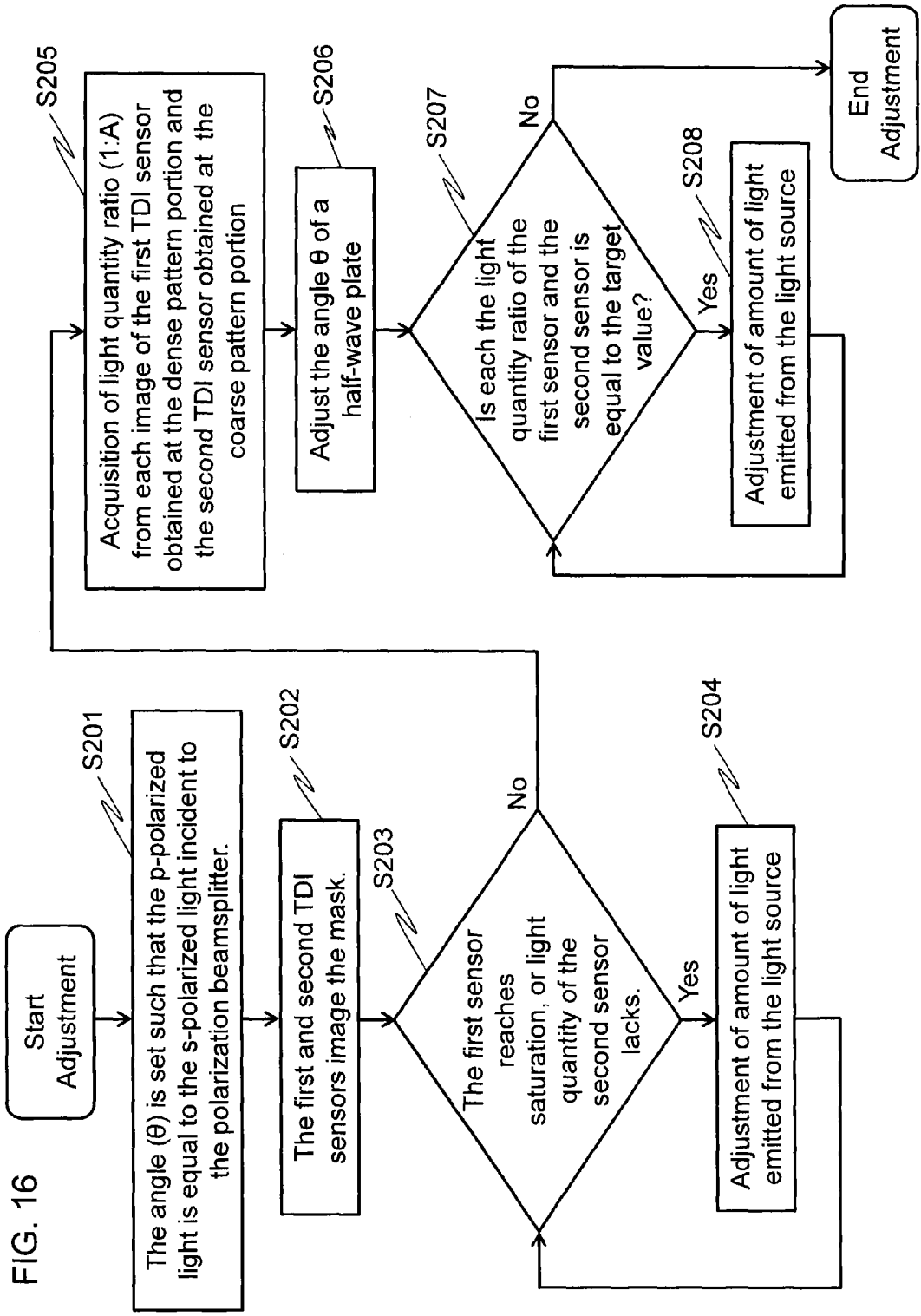
FIG. 16 is a flowchart illustrating a method for adjusting light quantity of a light source and angle of a half-wave plate according to the third embodiment.

FIG. 16 is a flowchart illustrating a method for adjusting the light quantity of the light source 4001 and the angle of the half-wave plate 4005, and the method is a substantial part of the inspection method of the third embodiment.

Referring to FIG. 16, in 5201, the angle of the half-wave plate 4005 is set such that the quantity of p-polarized light (Lp) incident to the polarization beamsplitter 4006 in FIG. 15 is equal to the quantity of s-polarized light (Ls) incident to the polarization beamsplitter 4006.

The first and second sensors 4007 and 4008 image the pattern of the mask 4004 (S202).

(1) Whether the light quantity value of the first sensor 4007 reaches the saturation, or (2) whether the light quantity value of the second sensor 4008 is lacking, namely, whether the light quantity value of the second sensor 4008 does not reach the value enough to obtain the sufficient contrast is determined irrespective of the dense or coarse pattern (S203). When one of the conditions (1) and (2) is satisfied, the flow goes to S204 to adjust the light quantity introduced to the optical system from the light source 4001 in FIG. 15. Then, the flow returns to S203, and the processes in S203 and S204 are repeated until both the conditions (1) and (2) are not satisfied.

When both the conditions (1) and (2) are not satisfied in S203, the flow goes to S205. In S205, the light quantity ratio (1/A) of the second sensor 4008 to the first sensor 4007 is obtained from the dense pattern area imaged with the first sensor 4007 and the coarse pattern area imaged with the second sensor 4008.

Using the relationship between the angle of the half-wave plate 4005 and the light quantity ratio (1/A), the angle of the half-wave plate 4005 is adjusted to the angle θ such that the light quantity ratio of the second sensor 4008 to the first sensor 4007 becomes A:1 (S206).

As a result of the determination in S207, when each of the light quantity values of the first and second sensors 4007 and 4008 is much larger or smaller than the target value, the flow goes to 5208 to adjust the light quantity introduced to the optical system from the light source 4001. Then, the flow returns to S207, and the processes in S207 and 5208 are repeated until each light quantity value reaches the target value. The series of adjusting processes is ended after each of the light quantity values of the first and second sensors 4007 and 4008 reaches the target value.

Through the above processes, the first sensor 4007 can image the pattern with the light quantity value suitable for the dense pattern area, and the second sensor 4008 can image the pattern with the light quantity value suitable for the coarse pattern area.

An inspection apparatus according to the present embodiment will be described below.

Figure 17:
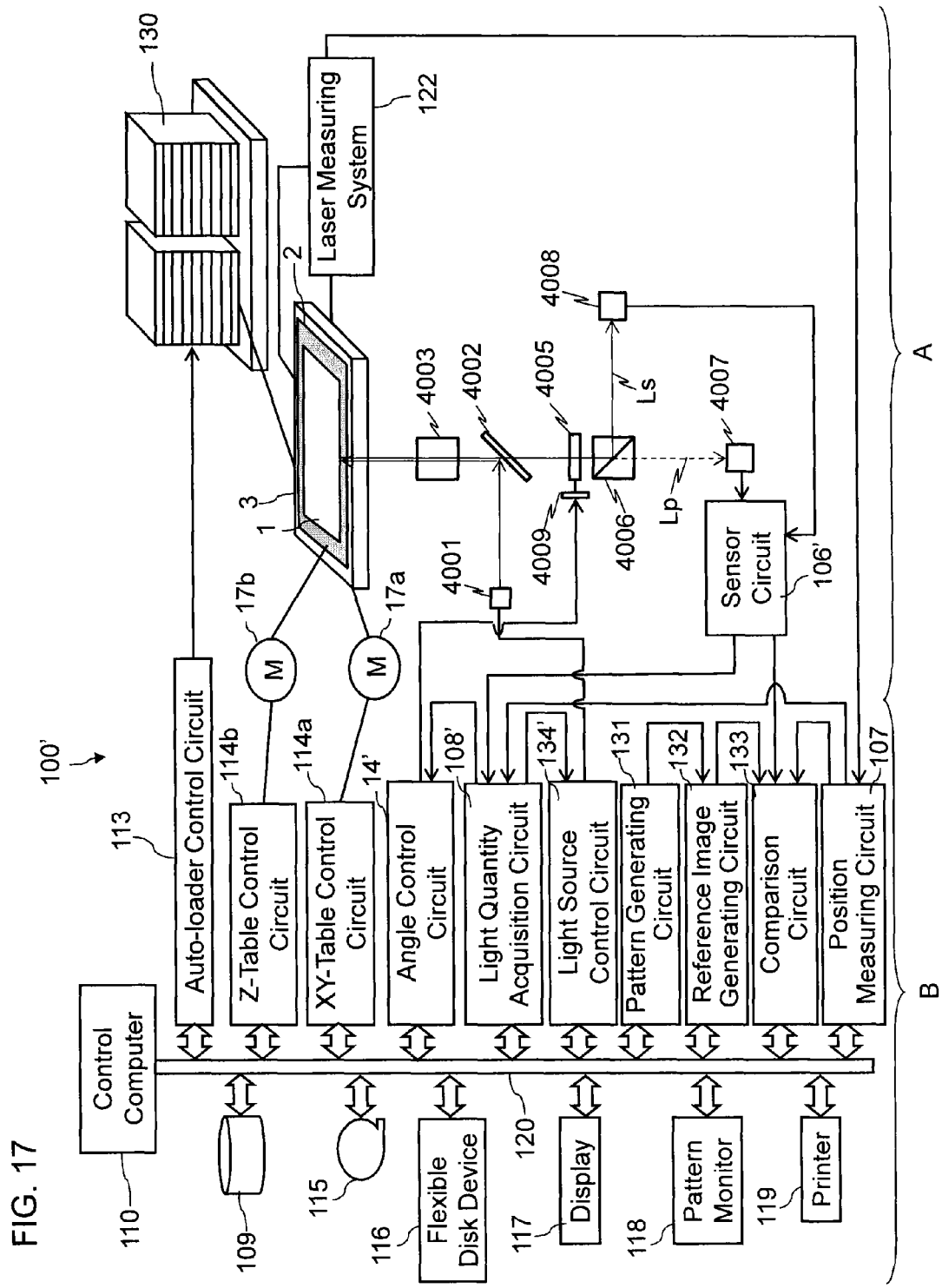
FIG. 17 is a configuration diagram of the inspection apparatus according to the third embodiment.

FIG. 17 is a configuration diagram of an inspection apparatus 100' according to the present embodiment. In FIG. 17, the same component as that in FIG. 11 is designated by the same numeral. Although the components necessary in the third embodiment are illustrated in FIG. 17, another well-known component necessary for the inspection may be included. The die-to-database inspection method is described in the third embodiment by way of example. On the other hand, in the die-to-die inspection method, one of the optical images of the same patterns located in different regions in the surface of the inspection target is dealt with as the standard image.

As illustrated in FIG. 17, an inspection apparatus 100' includes a configuration unit A that constitutes an optical image acquisition unit and a configuration unit B that performs processing necessary for an inspection using an optical image acquired by the configuration unit A.

The configuration unit A includes the optical system as shown in FIG. 16. Moreover, otherwise, it includes an XY-table 3 that is movable in a horizontal direction (an X direction and a Y direction), a sensor circuit 106', a laser measuring system 122, and an auto-loader 130. The XY-table 3 may have a structure movable in a rotation direction.

In the configuration unit A, the optical image of the sample 1 that is an inspection target is acquired. The optical image data is an image of a mask in which a figure pattern is written based on graphic data included in design pattern data of the sample 1. For example, the optical image data is 8-bit data with no code, and expresses a gradation of brightness of each pixel.

A sample 1 that is the inspection target is placed on a Z-table 2. The Z-table 2 is provided on the XY-table 3, and is horizontally movable together with the XY-table 3.

The mask or the wafer may be used as the sample 1. In the present invention, the EUV mask is particularly suitable for the sample 1. A predetermined pattern such as a line and space pattern is provided in the sample 1. In the case that the sample 1 is the EUV mask in FIG. 3, the absorbing layer 5 on the reflecting layer 3 is the patterned layer. The density of the pattern provided in the sample 1 is not constant. Such a region as a memory mat portion of a semiconductor chip, where the pattern density is high, and such a region as a peripheral circuit portion of the semiconductor chip, where the pattern density is low, are mixed in the pattern.

Preferably the sample 1 is supported at three points using support members provided in the Z-table 2. In the case that the sample 1 is supported at four points, it is necessary to adjust a height of the support member with high accuracy. Unless the height of the support member is sufficiently adjusted, there is a risk of deforming the sample 1. On the other hand, in the three-point support, the sample 1 can be supported while the deformation of the sample 1 is suppressed to the minimum. The supporting member is configured by using a ballpoint having a spherical head surface. For example, the two support members in the three support members are in contact with the sample 1 at two corners, which are not diagonal but adjacent to each other in four corners of the sample 1. The remaining support member in the three support members is disposed in the region between the two corners at which the two other support members are not disposed.

The light source 4001 emits the light to the sample 1 in order to acquire the optical image of the sample 1. For example, a laser beam source that emits linearly-polarized light can be used as the light source 4001.

After the linearly-polarized light emitted from the light source 4001 is reflected by the half mirror 4002, the sample 1 that is the inspection target is illuminated with the light through the objective lens 4003. Then the light reflected by the sample 1 is incident to the imaging optical system through the objective lens 4003 and the half mirror 4002.

The half-wave plate 4005, the polarization beamsplitter 4006, the first sensor 4007, and the second sensor 4008 are provided in the imaging optical system. For example, the line sensor in which the CCD cameras are arrayed in line is used as the first and second sensors 4007 and 4008. The TDI sensor can be cited as an example of the line sensor.

The linearly-polarized light emitted from the light source 4001 is incident to the polarization beamsplitter 4006 while the phase of the linearly-polarized light is rotated by 90° using the half-wave plate 4005. At this point, the angle of the half-wave plate 4005 is set such that the amount of p-polarized light (Lp) incident to the polarization beamsplitter 4006 is equal to the amount of s-polarized light (Ls) incident to the polarization beamsplitter 4006. The polarization beamsplitter 4006 transmits the p-polarized light component (Lp) while reflecting the s-polarized light component (Ls). The polarizing filter except the polarization beamsplitter 4006 may be used as long as the polarizing filter separates the incident light with the polarized light components.

The p-polarized light (Lp) reflected by the sample 1 is incident to the first sensor 4007 through the polarization beamsplitter 4006. On the other hand, the s-polarized light (Ls) reflected by the sample 1 is reflected by the polarization beamsplitter 4006, and is incident to the second sensor 4008.

In the above optical system, the light reflected by the sample 1 is introduced to the sensor. Alternatively, the sample 1 is illuminated with the light from above, and the light transmitted through the sample 1 may be introduced to the sensor. A combination of the both can simultaneously obtain the optical images of the transmitted light and the reflected light.

In the controller B, a control computer 110 that controls the whole inspection apparatus 100' is connected to a position measuring circuit 107, a light quantity acquisition circuit 108' used as an example of the light quantity acquisition unit, the angle control circuit 14', a pattern generating circuit 131, a reference image generating circuit 132, a comparison circuit 133, a light source control circuit 134' used as an example of the light source controller, an auto-loader control circuit 113, a XY-table control circuit 114a, a Z-table control circuit 114b, a magnetic disk device 109, a magnetic tape device 115, and flexible disk device 116, which are examples of a storage device, a display 117, a pattern monitor 118, and a printer 119 through a bus 120 that constitutes a data transmission line.

In FIG. 17, a sensor circuit 106', the position measuring circuit 107, the light quantity acquisition circuit 108', the angle control circuit 14', the pattern generating circuit 131, the reference image generating circuit 132, the comparison circuit 133, the light source control circuit 134', the auto-loader control circuit 113, an XY-table control circuit 114a, and a Z-table control circuit 114b are constructed with electric circuits. However, the inspection apparatus 100' is not necessarily constructed with the electric circuits. Alternatively, at least some of the electric circuits may be replaced with software that can cause the control computer 110 to execute the similar processing. The inspection apparatus 100 may be constructed with a combination of the electric circuits and the software. As used herein, the "unit" is a concept including the "circuit", and may be constructed with a program running on a computer, a combination of hardware and software, or a combination of software and firmware as well as a program being software. In the case that the unit is constructed with the program, the program is recorded, for example, in the magnetic disk device 109.

The Z-table 2 is driven by the motor 17b controlled by the Z-table control circuit 114b. The XY-table 3 is driven by the motor 17a controlled by the XY-table control circuit 114a. For example, a stepping motor is used as each motor.

The control computer 110 controls the XY-table control circuit 114a and Z-table control circuit 114b to drive the XY-table 3 and Z-table 2. A moving position of the XYθ-table 102 is measured by the laser measuring system 122, and transmitted to the position measuring circuit 107.

The control computer 110 controls the auto-loader control circuit 113 to drive the auto-loader 130. The auto-loader 130 automatically conveys the sample 1, and automatically discharges the sample 1 after the inspection.

The design pattern data that is reference data of the die-to-database method is stored in the magnetic disk drive 109. In the progress of the inspection, the design pattern data is read and transmitted to the pattern generating circuit 131. In addition, the design pattern data is as having explained using FIG. 12 in the first embodiment.

In the pattern generating circuit 131, the design pattern data is converted into image data (bit pattern data).

The image data converted by the pattern generating circuit 131 is transmitted to the reference image generating circuit 132, that is, the reference image producing unit, and used to produce a reference image (also referred to as reference data).

The optical image data output from the sensor circuit 106' is transmitted to the comparison circuit 133 together with data indicating a position of the sample 1 on the XY-table 3. The data is output from the position measuring circuit 107. The reference image is also transmitted to the comparison circuit 133.

In the comparison circuit 133, the optical image data and the reference data are compared to each other using a proper comparison determination algorithm. In the configuration of FIG. 17, reflection images are compared to each other. In a configuration in which a transmission optical system is used, transmission images are compared to each other, or a comparison determination algorithm in which reflection and transmission are combined is used. As a result of the comparison, in the case that a difference between the two exceeds a predetermined threshold, the position is determined to be the defect.

Moreover, the optical image data is also transmitted to the light quantity acquisition circuit 108'. And the position measuring circuit 107 transmits the data indicating the position of the sample 1 on the XY-table 3 to the light quantity acquisition circuit 108'.

In the light quantity acquisition circuit 108', the optical image data is expressed by a gradation value in each pixel. For example, one of values from a 0 gradation level to a 255 gradation level is provided to each pixel using a gray scale having a 256-level gradation value. The light quantity values of the first sensor 4007 and the second sensor 4008 are obtained from the gradation values of the images captured with the first sensor 4007 and the second sensor 4008, and the light quantity ratio (1/A) of the second sensor 4008 to the first sensor 4007 is obtained from the light quantity values. Then, the relationship between the angle of the half-wave plate 4005 and the light quantity ratio (1/A) is obtained, and the angle θ is obtained from the relationship such that the light quantity ratio of the second sensor 4008 to the first sensor 4007 becomes A:1.

The information on the angle θ obtained by the light quantity acquisition circuit 108' is transmitted to the angle control circuit 14'. The angle control circuit 14' controls the angle of the half-wave plate 4005. Specifically, the angle control circuit 14' controls a rotating mechanism 4009 provided in the half-wave plate 2002 such that the light quantity ratio of the second sensor 4008 to the first sensor 4007 becomes A:1, thereby adjusting the angle of the half-wave plate 4005.

The pattern of the sample 1 is imaged with the first sensor 4007 and the second sensor 4008 after the angle of the half-wave plate 4005 is adjusted. The light quantity values of the first sensor 4007 and the second sensor 4008 are obtained by the light quantity acquisition circuit 108'. In the case that each of the light quantity values is much larger or smaller than the target value, the light quantity acquisition circuit 108' transmits a signal to the light source control circuit 134'.

According to an instruction from the light quantity acquisition circuit 108', the light source control circuit 134' adjusts the light quantity introduced to the optical system from the light source 4001 such that each of the light quantity values of the first sensor 4007 and the second sensor 4008 becomes the target value. Therefore, the first sensor 4007 can perform the imaging with the light quantity value suitable for the dense pattern area, and the second sensor 4008 can perform the imaging with the light quantity value suitable for the coarse pattern area.

An example of a method for inspecting the sample 1 with the inspection apparatus 100' of FIG. 17 will be described below.

(Process of Adjusting Angle of Half-Wave Plate and Light Quantity of Light Source)

The angle of the half-wave plate 4005 is adjusted such that the light quantity value of the first sensor 4007 is suitable for the dense pattern area and such that the light quantity value of the second sensor 4008 is suitable for the coarse pattern area. The light quantity of the light source 4001 is also adjusted. The adjustment is performed as follows.

The pattern of the sample 1 is imaged with the first sensor 4007 and the second sensor 4008. Although the whole pattern of the sample 1 is not necessarily imaged, at least the dense pattern area and the coarse pattern area are imaged. Not the pattern of the sample 1 that is the inspection target but the pattern of the mask that is a previously-fixed standard may be used.

The light quantity values of the first sensor 4007 and the second sensor 4008 are obtained from gradation values of the images captured with the first sensor 4007 and the second sensor 4008. The light quantity ratio (1/A) of the second sensor 4008 to the first sensor 4007 is obtained from the light quantity values. Then the relationship between the angle of the half-wave plate 4005 and the light quantity ratio (1/A) is obtained, and the angle θ is obtained from the relationship such that the light quantity ratio of the second sensor 4008 to the first sensor 4007 becomes A:1.

The information on the angle θ obtained by the light quantity acquisition circuit 108' is transmitted to the angle control circuit 14'. The angle control circuit 14' controls the angle of the half-wave plate 4005. That is, the angle control circuit 14' controls the rotating mechanism 4009 provided in the half-wave plate 4005 such that the light quantity ratio of the second sensor 4008 to the first sensor 4007 becomes A:1, thereby adjusting the angle of the half-wave plate 4005.

The pattern of the sample 1 is imaged with the first sensor 4007 and the second sensor 4008 again after the angle of the half-wave plate 4005 is adjusted. The light quantity values of the first sensor 4007 and the second sensor 4008 are obtained by the light quantity acquisition circuit 108'. The light quantity of the light source is adjusted in the case that each of the light quantity values is much larger or smaller than the target value.

Specifically, the light quantity acquisition circuit 108' transmits the signal to the light source control circuit 134'. According to the instruction from the light quantity acquisition circuit 108', the light source control circuit 134' adjusts the light quantity introduced to the optical system from the light source 4001 such that each of the light quantity values of the first sensor 4007 and the second sensor 4008 becomes the target value. Therefore, the first sensor 4007 can perform the imaging with the light quantity value suitable for the dense pattern area, and the second sensor 4008 can perform the imaging with the light quantity value suitable for the coarse pattern area.

(Optical Image Acquisition Process)

As described above, by adjusting the angle of the half-wave plate 4005 and the light quantity of the light source 4001, the light quantity value of the first sensor 4007 is suitable for the dense pattern area, and the light quantity value of the second sensor 4008 is suitable for the coarse pattern area. At this point, the optical image for the inspection is obtained.

In the optical image acquisition process of the third embodiment, the configuration unit A of FIG. 17 acquires the optical image of the sample 1. Because the specific acquisition procedure is similar to that of the first embodiment, the description is omitted.

The first sensor 4007 and the second sensor 4008 performs the photoelectric conversion to the pattern image formed on the first sensor 4007 and the second sensor 4008 in FIG. 11, and the sensor circuit 106' performs the A/D (analog-digital) conversion to the pattern image. Then the optical image is transmitted from the sensor circuit 106' to the comparison circuit 133.

(Reference Image Generation Process)

(1) Storage Process

In the case of inspection by the die-to-database comparison method, the reference image generated from the design pattern data becomes a reference of the defect determination. In the inspection apparatus 100', the design pattern data used to form the pattern in the sample 1 is stored in the magnetic disk drive 109.

(2) Pattern Generating Process

In the pattern generating process, the pattern generating circuit 131 of FIG. 17 reads the design pattern data from the magnetic disk drive 109 through the control computer 110, and converts the read design pattern data of the sample 1 into the binary or multi-value image data (design image data). The image data is transmitted to the reference image generating circuit 132.

(3) Filtering Process

In the filtering process, the reference image generating circuit 132 of FIG. 17 performs the proper filtering to the design pattern data, that is, the graphic image data. The learning process of the filter coefficient may be performed using the pattern of the mask that is the reference fixed in the production process or a part of the pattern of the sample 1 that is the inspection target. In the latter case, the filter coefficient is acquired in consideration of the pattern line width of the region used in the learning process or a finished degree of the roundness of the corner, and reflected in a defect determination criterion of the whole mask. In the case that the sample 1 that is the inspection target is used, advantageously the learning process of the filter coefficient can be performed without removing influences such as a variation of production lot and a fluctuation in condition of the inspection apparatus. However, when the dimension fluctuates in the surface of the sample 1, the filter coefficient becomes optimum with respect to the position used in the learning process, but the filter coefficient does not necessarily become optimum with respect to other positions, which results in a pseudo defect. Therefore, preferably the learning process is performed around the center of surface of the sample 1 that is hardly influenced by the fluctuation in dimension. Alternatively, the learning process is performed at multiple positions in the surface of the sample 1, and the average value of the obtained multiple filter coefficients may be used.

(Comparison Process)

Because the angle of the half-wave plate 4005 and the light quantity of the light source 4001 are adjusted, the first sensor 4007 becomes the light quantity value suitable for the dense pattern area, and the second sensor 4008 becomes the light quantity value suitable for the coarse pattern area. Therefore, the image captured with the first sensor 4007 is used to inspect the dense pattern area, and the image captured with the second sensor 4008 is used to inspect the coarse pattern area.

The optical image data obtained through the optical image acquisition process is transmitted to the comparison circuit 133. At this point, the optical image data includes the data imaged by the first sensor 4007 and the data imaged by the second sensor 4008. The reference image generating circuit 132 transmits the reference data to the comparison circuit 133.

In the comparison circuit 133, the optical image data and the reference image data are compared to each other by the die-to-database method. Specifically, the imaged stripe data is cut out in units of inspection frames, and is compared to the data that is a defect criterion in each inspection frame using a comparison determination algorithm. At this point, for the dense pattern area of the sample 1, the optical image data imaged with the first sensor 4007 is compared to the reference data. On the other hand, for the coarse pattern area of the sample 1, the optical image data imaged with the second sensor 4008 is compared to the reference data.

As a result of the comparison, the place where a difference between the optical image data and the reference data exceeds a predetermined threshold is determined to be the defect. The information on the defect is stored as a mask inspection result. For example, the control computer 110 stores a coordinate of the defect and the optical image warranting the defect determination as the mask inspection result in the magnetic disk device 109.

After that, the mask inspection result is transmitted to a review tool. A review process is an operation in which the operator determines whether the detected defect will become a practical problem. The defect information determined through the review process is also stored in the magnetic disk drive 109 of FIG. 17. When the defect to be corrected is confirmed by the review tool, the sample 1 is transmitted to a repair apparatus 600, that is, the external device of the inspection apparatus 100' together with a defect information list. Because a correction method depends on whether the defect is projected or recessed, a defect type including the distinction between the projection and the recess and the defect coordinate are added to the defect information list.

As described above, in the third embodiment, because the polarization beamsplitter is arranged in the imaging optical system to branch the light immediately before the first and second sensors, the light incident to each of the first and second sensors can easily be controlled. Also in the third embodiment, by adjusting the angle of the half-wave plate and the light quantity of the light source, the light quantity value of the first sensor is suitable to obtain the image of the dense pattern area, and the light quantity value of the second sensor is suitable to obtain the image of the coarse pattern area. The image captured with the first sensor is used to inspect the dense pattern area, and the image captured with the second sensor is used to inspect the coarse pattern area. Therefore, the inspection apparatus and the inspection method for being able to accurately inspect both the dense pattern area and the coarse pattern area are provided.

The present invention is not limited to the embodiments described and can be implemented in various ways without departing from the spirit of the invention.

For example, the half-wave plate and the branching element of the first to third embodiments and the quarter-wave plate of the second embodiment may be detachable from the inspection apparatus. When the half-wave plate, the branching element, and the quarter-wave plate are detached from the inspection apparatus, the light reflected by or transmitted through the sample that is the inspection target is not branched but is incident to one of the first and second sensors. Accordingly, the inspection apparatus having this configuration can be used in the case that the sample that is not necessary to acquire the plural optical images according to the pattern density to compare the optical images to the standard images, for example, the mask in which the pattern is not too fine is inspected. In this case, preferably a driving mechanism is provided in the inspection apparatus in order to move the half-wave plate, the branching element, and the quarter-wave plate, more preferably the driving mechanism can be controlled by the control computer of the inspection apparatus.

The above description of the present embodiment has not specified apparatus constructions, control methods, etc., which are not essential to the description of the invention, since any suitable apparatus construction, control methods, etc. can be employed to implement the invention. Further, the scope of this invention encompasses all inspection apparatus and inspection method employing the elements of the invention and variations thereof, which can be designed by those skilled in the art.

What is claimed is:

1. An inspection apparatus comprising:
  a light source configured to emit light with which a sample is illuminated;
  a half-wave plate configured to transmit the light emitted from the light source;
  a branching element configured to branch the light transmitted through the half-wave plate;
  a first sensor and a second sensor configured to acquire an optical image of a pattern formed in the sample, sensing the branched light incident on the first sensor and the second sensor;
  a light quantity acquisition unit configured to acquire a light quantity ratio (1:A) of the second sensor to the first sensor using the optical image, and to obtain an angle $\theta$ of the half-wave plate such that the light quantity ratio becomes A:1;
  an angle controller configured to receive information on the angle $\theta$ from the light quantity acquisition unit to control an angle of the half-wave plate;
  a light source controller configured to receive information on each of light quantity values of the first sensor and the second sensor from the light quantity acquisition unit, and to control a light quantity of the light source such that each of the light quantity values becomes a target value; and
  a comparator configured to compare the optical image acquired by the first sensor to a standard image with respect to a pattern having a density of a predetermined value or more in the pattern, to compare the optical image acquired by the second sensor to the standard image with respect to a pattern having a density smaller than the predetermined value in the pattern, and to determine a place where a difference between the optical image acquired by the first sensor and the standard image or a difference between the optical image acquired by the second sensor and the standard image exceeds a threshold to be a defect.

2. The inspection apparatus according to claim 1, wherein the branching element branches the light with which the sample is illuminated.

3. The inspection apparatus according to claim 1, further comprising a quarter-wave plate,
wherein the sample is illuminated with the light, which is transmitted through the quarter-wave plate after transmitted through the branching element.

4. The inspection apparatus according to claim 3, wherein the half-wave plate, the branching element, and the quarter-wave plate are configured to be detachable.

5. The inspection apparatus according to claim 1, wherein the branching element branches the light reflected by or transmitted through the sample.

6. The inspection apparatus according to claim 5, wherein the half-wave plate transmits the light reflected by or transmitted through the sample.

7. An inspection method comprising the steps of:
illuminating a sample that is an inspection target with light, which is emitted from a light source and transmitted through a half-wave plate, after the light is branched, causing the light reflected by or transmitted through the sample to impinge on a first sensor and a second sensor, and adjusting a light quantity of the light source (1) when a light quantity of the first sensor reaches saturation or (2) when a light quantity of the second sensor is lower than a predetermined value;

acquiring an optical image of a pattern formed in the sample using the first sensor and the second sensor when both the condition (1) and the condition (2) are not satisfied;

acquiring a light quantity ratio (1:A) of the second sensor to the first sensor using the optical image, and obtaining an angle θ of the half-wave plate such that the light quantity ratio becomes A:1;

adjusting an angle of the half-wave plate to the angle θ;

controlling the light quantity of the light source such that each of light quantity values of the first sensor and the second sensor becomes a target value;

acquiring the optical image of the pattern formed in the sample using the first sensor and the second sensor after the angle of the half-wave plate is adjusted to the angle θ and after each of the light quantity values of the first sensor and the second sensor becomes the target value; and comparing the optical image acquired by the first sensor to a standard image with respect to a pattern having a density of a predetermined value or more in the pattern, comparing the optical image acquired by the second sensor to the standard image with respect to a pattern having a density smaller than the predetermined value in the pattern, and determining a place where a difference between the optical image acquired by the first sensor and the standard image or a difference between the optical image acquired by the second sensor and the standard image exceeds a threshold to be a defect.

8. An inspection method comprising the steps of:
illuminating a sample that is an inspection target with light emitted from a light source, causing the light to impinge on a first sensor and a second sensor after the light, which is reflected by or transmitted through the sample and transmitted through a half-wave plate, is branched, and adjusting a light quantity of the light source (1) when a light quantity of the first sensor reaches saturation or (2) when a light quantity of the second sensor is lower than a predetermined value;

acquiring an optical image of a pattern formed in the sample using the first sensor and the second sensor when both the condition (1) and the condition (2) are not satisfied;

acquiring a light quantity ratio (1:A) of the second sensor to the first sensor using the optical image, and obtaining an angle θ of the half-wave plate such that the light quantity ratio becomes A:1;

adjusting an angle of the half-wave plate to the angle θ;

controlling the light quantity of the light source such that each of light quantity values of the first sensor and the second sensor becomes a target value;

acquiring the optical image of the pattern formed in the sample using the first sensor and the second sensor after the angle of the half-wave plate is adjusted to the angle θ and after each of the light quantity values of the first sensor and the second sensor becomes the target value; and comparing the optical image acquired by the first sensor to a standard image with respect to a pattern having a density of a predetermined value or more in the pattern, comparing the optical image acquired by the second sensor to the standard image with respect to a pattern having a density smaller than the predetermined value in the pattern, and determining a place where a difference between the optical image acquired by the first sensor and the standard image or a difference between the optical image acquired by the second sensor and the standard image exceeds a threshold to be a defect.

* * * * *